United States Patent [19]

Imam et al.

[11] Patent Number: 5,658,743
[45] Date of Patent: Aug. 19, 1997

[54] ANTIBODY TO ANTIGEN SPECIFICALLY EXPRESSED ON THE SURFACE OF B CELLS AND HODGKIN'S CELLS

[75] Inventors: Ashraf Imam, North Hollywood; Clive R. Taylor, South Pasadena, both of Calif.

[73] Assignee: University of Southern California, Los Angeles, Calif.

[21] Appl. No.: 229,364

[22] Filed: Apr. 18, 1994

Related U.S. Application Data

[62] Division of Ser. No. 994,082, Dec. 16, 1992, Pat. No. 5,304,635, which is a continuation of Ser. No. 492,542, Mar. 12, 1990, abandoned.

[51] Int. Cl.⁶ .......................... G01N 33/53; G01N 33/574
[52] U.S. Cl. .................. 435/7.21; 435/7.23; 435/7.9; 435/326; 435/330; 435/332; 435/343.1; 435/344; 436/64; 436/63; 530/387.1; 530/387.7; 530/388.1; 530/388.73; 530/388.8
[58] Field of Search .................... 435/7.21, 7.9, 435/7.23, 70.21, 240.27, 960, 975; 436/548, 813, 63, 64; 530/387.1, 387.7, 388.1, 388.73, 388.8

[56] References Cited

U.S. PATENT DOCUMENTS 4,861,581  8/1989  Epstein et al. .................. 424/1.49

OTHER PUBLICATIONS

Harlow, E. et al. Antibodies: A Laboratory Manual. Cold Spring Harbor, NY: Cold Spring Harbor Laboratory 1988.
Agnarsson, et al.; *Am.J.Sur.Path.* 12(4):264–274 (1988).
Epstein, et al.; *J. Immunol.* 133(2): 1028–1036 (1984).
Hecht et al.; *J. Immunol.* 134(6): 4231–4236 (1985).
Hsu et al.; *A.J.C.P.* 82: 29–32 (1984).
Hsu et al., *JNCI* 77(2): 363–370 (1986).
Imam et al., *Annals of the New York Academy of Sciences* 551: 363–365 (1988).
Imam et al., *Cancer Research* 50: 1650–1657 (1990).
O'Conner et al., *Histopathology* 11: 733–740 (1987).
Pawlak–Byczkowska et al., *Cancer Res.* 49: 4568–4577 (1989).
Pinkus et al., *A.J.P.* 119(2): 244–251 (1985).
Schwab et al., *Nature* 299: 65–67 (1982).
Sherrod et al., *Cancer* 57: 2135–2140 (1986).
Stein et al., *Int.J.Cancer* 28: 425–429 (1981).
Stein et al., *Int.J.Cancer* 29: 283–290 (1982).
Stein et al., *Int.J.Cancer* 30: 445–459 (1982).
Taylor, Clive R.; "Hodgkin's Disease and the Lymphomas"; vol. 4 34–48, in Annual Research Review Series, Horrobin, D.F. Ed., Eden Press, Inc. (1980).
Taylor, Clive R.; *Recent Results Cancer Research* 64:214–231 (1978).
Taylor, Clive R.; "Upon the Enigma of Hodgkins Disease and the Reed–Sternberg Cell" in Controversies in the Management of Lymphomas II., Bennet, J.M. ed., Martinuss Nijhoff Publishers, Boston, pp. 91–110 (1983).
Weiss et al., *Human Pathology* 19 (8): 967–973 (1988).
Della Croce, et al., "Anti–Bla.36 Monoclonal Antibody Shows Reactivity with Hodgkin's Cells and B Laymphocytes in Frozen and Paraffin–Embedded Tissues", Hematological Oncology, vol. 9, pp. 103–114 (1991).

*Primary Examiner*—Toni R. Scheiner
*Assistant Examiner*—Yvonne Eyler
*Attorney, Agent, or Firm*—Knobbe Martens Olson & Bear

[57] ABSTRACT

The invention relates to a new antigen termed BLA-36 specifically expressed on the surface of Hodgkin's cells, Reed-Sternberg cells and B lymphocytes, and to a new monoclonal antibody (anti-BLA-36) specific thereto. The antigen is characterized by the following properties:

a molecular weight of about 36,000 D;
  the presence of an epitope recognized by antibody to said protein;
  specific expression by Hodgkin's cells and Reed-Sternberg cells in all subsets of Hodgkin's disease, and by activated and early proliferating B cells;
  no expression by T cells;
  capability of reacting with its antibody in both frozen and fixed/paraffin embedded tissues;
  a function associated with the growth of cells capable to express said antigen protein.

14 Claims, 8 Drawing Sheets

ANTIBODY TO ANTIGEN SPECIFICALLY EXPRESSED ON THE SURFACE OF B CELLS AND HODGKIN'S CELLS

RELATED APPLICATIONS

This application is a divisional of application Ser. No. 07/994,082, filed Dec. 16, 1992, U.S. Pat. No. 5,304,635, which is a continuation of application Ser. No. 07/492,542, filed Mar. 12, 1990, abandoned.

FIELD OF THE INVENTION

The present invention relates to a new antigen, termed BLA-36, specifically expressed on the surface of Hodgkin's cells, Reed-Sternberg cells and B lymphocytes, and to a new monoclonal antibody (anti-BLA-36) specific thereto. By detecting BLA-36 in human tissues, using anti-BLA-36 antibody, Hodgkin's disease and early B cell lymphomas can be diagnosed, imaged and treated by radioimmuno-therapy.

BACKGROUND OF THE INVENTION

Hodgkin's disease is a malignant lymphoma of mixed cell type which is usually classified according to the Lukes-Butler classification [Lukes et al., *Cancer Res.* 26, 1311 (1966)]. Cases of Hodgkin's disease of all four major histologic subtypes (lymphocyte predominance, mixed cellularity, lymphocyte depleted, and nodular sclerosis) contain variable numbers of cells that characterize the Hodgkin's disease process. The largest and most characteristic of these cells are termed Reed-Sternberg cells. The cell is typically binucleate, multinucleate, or has a polylobulated nucleus. Mononuclear variants of this cell are termed Hodgkin's cells. Morphological and immunohistochemical studies suggest that lymphocyte predominant Hodgkin's disease is a B-cell neoplasm and as such is distinct from other subtypes of Hodgkin's disease [see e.g. Pinkus, G. S. and Said, J. W., *Am. J. Pathol.* 133, 211–217 (1988); Burns et al., *Am. J. Surg. Pathol.* 8, 253–261 (1984); Hansmann et al., *J. Cancer Res. Clin. Oncol.* 114, 405–410 (1988)]. The cellular derivation of other types of Hodgkin's disease remains controversial.

The non-Hodgkin lymphomas are traditionally classified by standard histologic methods. However, since this classification provides little information about the origin or biology of these tumors, recently immunologic classification, emphasizing the principal immunologic cell type in the lymphoma, is favored. B cell-type lymphomas are at present classified according to the microscopic features of the cells, especially the nuclei. These are thought to represent different stages of differentiation of B cells between stem cells and plasma cells [see "Basic & Clinical Immunology" 3rd Edition, Fundenberg, H. H., Stites, D. P., Caldwell, J. L., Wells, J. V., Eds., Los Altos, Calif., 1980, Chapter 31]. The summary of an NCI-sponsored study of classification of non-Hodgkin's lymphomas was published in *Cancer* 49, 2112–2135 (1982).

The development of Hodgkin's and various B cell lines has permitted the production of monoclonal antibodies against such cell lines, and the identification of antigen molecules recognized by the antibodies.

The Fourth International Workshop of Leukocyte Differentiation Antigens (1989) listed no less than 78 major cluster designations (CDs 1–78) for leukocyte antigens, with several CDs including more than one related antigens (e.g. CD11A, CD11B, CD11C, etc.). The molecular weights of the majority of these antigens have been defined. Of the 78 different CD antigens, approximately one dozen show some specificity for B cells (e.g. CDs 19–24, CD32, CD37, CD40, CDs 73–77). Only a minority of these show restricted specificity for B cells, and most are expressed on a limited number of other cell types.

Antigens that show some preferential expression on Reed-Sternberg cells and their mononuclear variants, Hodgkin's cells, in Hodgkin's disease include CD15, CD30, and CD74. CD15 was detected by antibody LeuM1, CD30 by antibody Ki-1 and related antibodies, and CD74 by antibody LN2. LeuM1 is, for example, described in the following publications: Hsu and Jaffe, *Am. J. Clin. Pathol.* 82, 29–32 (1984); Pinkus et al., *Am. J. Pathol.* 119, 244–252 (1985); and Hsu et al., *JNCI* 77, 363–370 (1986). Ki-1 and related antibodies are disclosed in numerous scientific publications, including Schwab et al., *Nature* 299, 65–67 (1982); Stein et al., *Int. J. Cancer.* 30, 445–449 (1982); O'Connor et al., *Histopathology* 11, 733–740 (1987). Articles concerning antibody LN2 include Epstein et al., *J. Immunol.* 133, 1028–1036 (1984) and Sherrod et al., *Cancer* 57, 2135–2139 (1986).

A further anti-Reed-Sternberg cell antibody, HeFi-1 is disclosed by Hecht et al., *J, Immunol.* 134, 4231–4236 (1985).

All of these antibodies identify only a portion of Reed-Sternberg cells in some of the subsets of Hodgkin's disease, and their specificity is not satisfactory. For example, upon more extensive study, the reactivity of Ki-1 appears not to be restricted to Reed-Sternberg cells, but includes the malignant cells of some of the non-Hodgkin's lymphomas, as well as a subset of apparently normal cells, the identity of which is not yet known, but which show some features of myeloid cells [Stein et al., *Int. J. Cancer* 29, 283–290 (1982)].

Monoclonal antibodies EPB-1 and EPB-2, reactive with human lymphoma, are described by Pawlak-Byczkowska et al., *Cancer Research* 49, 4568–4577 (1989). EPB-1 is reported to be specific to normal and malignant B cells and to Hodgkin's disease related cells, and is identified as having $IgG_1$ isotype. Its antigen has an estimated molecular weight of 35,000. The immunogen agent used to make EPB-1 was a B cell lymphoma.

Functional aspects of the antigen molecules recognized by any of these antibodies have not yet been reported. In addition, although there have been some sporadic reports describing the existence of inhibitory or cytotoxic factors in Hodgkin's disease [Taylor, C. R., "Hodgkin's Disease and the Lymphomas", Annual Research Reviews, D. Horrobin, Series ed. Churchill Livingston/Eden Press, London/New York, 1980], almost no information is available with respect to mechanisms of regulation of growth and differentiation of Hodgkin's or Reed-Sternberg cells, other than the general concept that the mononuclear Hodgkin's cell is the proliferating element from which the Reed-Sternberg cells are derived [Taylor, C. R., "Upon the enigma of Hodgkin's disease and the Reed-Stenberg cell." In: Controversies in the Management of Lymphomas II., J. M. Bennet, ed. Martinus Nijhoff Publishers, Boston, pp. 91–110, 1983; Taylor, C. R., *Recent Results Cancer Res.,* 64, 214–231 (1978)].

Immunophenotypic characterization of lymphomas by monoclonal antibodies has proved a valuable adjunct to histologic diagnosis and has facilitated understanding of the lineage of certain lymphomas.

Monoclonal antibodies detecting various antigens have been used or proposed for a number of purposes in research, and for diagnostic studies of leukemias and lymphomas in men and animals. The techniques employed include:

1. Leukocyte identification by phenotype, utilizing flow cytometry, immunofluorescence, immunoenzyme techniques, or immuno electron microscopy.

2. Leukocyte separation techniques, including flow cytometry and panning.
3. Identification and classification of leukemias.
4. Radioimmunimaging of lymphomas in animals and man.
5. Radioimmunotherapy of lymphomas in animals and man.
6. Studies of leukocyte differentiation, maturation and function in experimental models and human disease.

However, the vast majority of the antibodies described to date recognize epitopes that are sensitive to the process of fixation or embedment in paraffin wax. Such antibodies detect their corresponding antigens only in frozen sections exposed to minimal fixation (such as 10 seconds in acetone), and do not detect the corresponding antigens following formalin or B5 fixation and embedment in paraffin. This fact hampers the utilization of many of these antibodies for diagnostic purposes in which only fixed and paraffin embedded sections are available. Thus, particular diagnostic importance is attached to those antibodies that reliably detect their corresponding antigens in fixed tissues. Since this fact has been realized, the number of such antibodies available has been increased, but still constitutes only a small minority overall.

Accordingly, for successful diagnosis of lymphomas, antibodies that are sufficiently specific to the lymphoma to be identified, and detect the corresponding antigens following fixation and embedment in paraffin, are required.

With regard to the identification of Hodgkin's disease, of the above-mentioned antibodies LeuM1 and LN2 are both reactive in paraffin embedded tissues. Antibodies related to Ki-1 which are effective in paraffin embedded tissues, also have become available. However, as hereinabove mentioned, all three of these antibodies identify only a portion of Reed-Sternberg cells in some of the subsets of Hodgkin's disease. None of them identify Reed-Sternberg cells in all cases of Hodgkin's disease. EPB-1 is also reported to remain active after fixation and paraffin embedment, and appears to have a better specificity to B cells and Hodgkin's disease related cells than any of the earlier published antibodies.

However, there is no disclosure of the functional aspects of the antigens identified by any of these antibodies on Reed-Sternberg and Hodgkin's cells. Whereas the literature contains many reports describing the existence of inhibitory or cytotoxic factors in the serum of patients with Hodgkin's disease, the corresponding antigens have not been identified and little information is available with respect to the mechanisms of regulation of growth and differentiation of Hodgkin's or Reed-Sternberg cells.

There is a great need for monoclonal antibodies with specificity and high reactivity to Reed-Sternberg cells, which retain their immunoreactivity in tissues that have been fixed and embedded in paraffin. Such antibodies would have wide applications, since paraffin sections remain the standard in diagnostic histopathology, based upon convenience, safety, superior morphology preservation, and economic factors. Additionally, it would be desirable to identify antigen(s) specifically expressed on Hodgkin's disease related cells, which have regulatory functions in the growth and/or differentiation of such cells. Study of the function of such antigens would be an invaluable tool in understanding and ultimately, treating Hodgkin's disease.

SUMMARY OF THE INVENTION

The goal of the present invention is to provide a monoclonal antibody with specificity for Reed-Sternberg cells which retains its immunoreactivity in tissues that are routinely fixed and embedded in paraffin. The specificity of such antibody enables its use in the diagnosis of Hodgkin's disease and, by its pattern of reactivity, may shed light on the cellular origin of the malignant cells of Hodgkin's disease. Furthermore, the availability of an antibody specific for Reed-Sternberg cells, leads to the characterization and isolation of the antigens involved, as a preliminary to determining their functional role.

According to the present invention, a hitherto unrecognized antigen specifically expressed on the surface of Hodgkin's and Reed-Sternberg cells and on activated and early proliferating B lymphocytes was identified using a newly developed monoclonal antibody produced by immunization of a Balb/c mouse with a Hodgkin's cell line (HDLM-3). To indicate its specificity and molecular weight (36,000), this antigen was termed "B lymphocyte antigen 36" (BLA-36); and the antibody is referred to as anti-BLA-36.

In one aspect, the present invention relates to substantially pure B lymphocyte antigen 36 (BLA-36).

In another aspect, the present invention relates to a substantially pure antigen protein having the following characteristics:

a molecular weight of about 36,000 Dalton;

the presence of an epitope recognized by antibody to the protein;

specific expression by Hodgkin's cells and Reed-Sternberg cells in all subsets of Hodgkin's disease, and by activated and early proliferating B cells;

no expression by T cells;

capability of reacting with its antibody in both frozen and fixed/paraffin embedded tissues;

a function associated with the growth of cells capable of the expression of this antigen protein.

The term "substantially pure" is used to indicate that the protein is substantially devoid of other proteins associated therewith in nature. "Substantially" means that such proteins cannot be detected by standard techniques conventionally used for the detection of proteins.

In a further aspect, the present invention relates to a monoclonal antibody or a fragment thereof having the following properties:

$IgG_3$ subtype;

reactivity with Hodgkin's cells and Reed-Sternberg cells in all subsets of Hodgkin's disease, and with activated and early proliferating B cells;

lack of reactivity with T cells;

capability of reacting with the corresponding antigen in both frozen and fixed/paraffin embedded tissues;

reversible, dose-dependent growth-inhibitory effect on cells capable of expressing the corresponding antigen.

In a still further aspect, the present invention relates to a method for the isolation of an antigen protein having the above properties from Reed-Sternberg cells, Hodgkin's cells or activated or early proliferating B cells, comprising the steps of:

disrupting the membranes of said cells;

preparing cell extract containing solubilized proteins;

contacting said extract with a monoclonal antibody specific to said protein;

separating the fraction containing protein reacting with said monoclonal antibody; and isolating said protein.

In a still further aspect, the present invention relates to monoclonal antibody or a fragment thereof specific to B lymphocyte antigen 36.

The present invention further relates to a hybridoma cell line producing antibody specific to B lymphocyte antigen 36.

In another aspect, the present invention relates to a method for detection of an antigen protein having the above properties in mammalian tissues or cells in order to diagnose Hodgkin's disease or B cell lymphoma, comprising the steps of:

obtaining monoclonal antibody that is specific to the antigen protein, contacting said antibody with tissue or cells obtained from a mammal to be diagnosed; and detecting the antigen protein, if present, as well as assay kit for performing such method.

The invention also relates to methods for imaging lesions characteristic of Hodgkin's disease, comprising the steps of:

obtaining monoclonal antibody specific to an antigen having the above properties, said antibody being labeled;

labeling said antibody;

contacting said labeled antibody with tissue obtained from a mammal; and imaging said label.

In another aspect, the present invention relates to a method for inhibiting the growth of Reed-Sternberg cells, Hodgkin's cells or activated or early proliferating B cells, comprising the step of contacting such cells with a growth-inhibiting amount of anti-BLA-36 antibody or a (Fab')$_2$ fragment thereof.

BRIEF DESCRIPTION OF THE INVENTION

FIG. 1 illustrates the reactivity of anti-BLA-36 with HDLM.3 (Hodgkin's cell line). Cytopreparations of the cell line were fixed with cold acetone and stained with anti-BLA-36. The antibody shows strong reactivity with the cell surface and cytoplasm (original magnification ×200).

FIG. 2 illustrates the reactivity of anti-BLA-36 with cells in B.5-fixed and paraffin-embedded tissue sections by an indirect immunohistological staining method. (A) Normal lymph node. Anti-BLA-36 shows reactivity (dark area) with follicular center and mantle zone B lymphocytes (original magnification ×125). (B) Lymph node from a patient with Hodgkin's disease. Reed-Sternberg cell variants show predominant surface activity with anti-BLA-36, as indicated by arrows (original magnification ×200) counter-stained with Mayer's hematoxylin.

FIG. 3 shows the results of immunoblotting of BLA-36 antigen. Following the separation of proteins from BLA-36-positive (Lane A, molecular weight standards, Bio/Rad Chemical Co., Richmond, Calif.; Lane B, HDLM.3; Lane C, RAJI; Lane D, NALM-1; Lane E, Hodgkin's disease-lymph node) and BLA-36-negative (Lane F, CEM; Lane G, SU-DHL-1) cell lines by sodium dodecyl sulfate-polyacrylamide gel electrophoresis (SDS-PAGE), the protein bands were electrophoretically transferred to nitrocellulose filter-paper. Each line containing the transferred bands was cut and incubated with either anti-BLA-36 (Lanes B to G) or an equivalent amount of the antibody preabsorbed with an extract of a BLA-36-positive cell line (Lane H) as described in Example 1.

FIG. 4 shows the comparison of antigens recognized by antibodies to BLA-36 and LN2 (CD75) by Western-immunoblot analysis. Following the separation of proteins from RAJI cell line (Burkitt's lymphoma) by SDS-PAGE, the protein bands were electrophoretically transferred to nitrocellulose filter-paper. Each lane containing the transferred bands was cut and incubated with antibodies to BLA-36 (Lane A) or LN2 (Lane E). Lanes B and C represent the strips containing the preabsorbed extracts of Raji cell line and tissue from a patient with Hodgkin's disease, respectively, with immobilized LN2 prior to the application of anti-BLA-36. Lane F contained the extract preabsorbed with immobilized anti-BLA-36 before the LN2 antibody was applied. Lanes D and G represent strips with extracts which were preabsorbed and subsequently reacted with antibodies BLA-36 and LN2, respectively. The lane on the extreme left represents the molecular weight standards.

FIG. 5 illustrates the titration of anti-BLA-36 antibody on cell growth. Hodgkin's cells (HDLM.3) were grown in triplicate at $1.6 \times 10^5$ cells per well of 24-well-culture plate in the presence of varying concentrations (0.12–4.0 mg per ml) of F(ab')$_2$ fragments of antibody to BLA-36. The cells were removed on day 4 and were counted with a hemacytometer and assessed for viability by trypan-blue-dye exclusion.

FIG. 6 shows the effect of anti-BLA-36 on cell growth. Hodgkin's cell line, HDLM.3 ($1.6 \times 10^5$ cells per well) was cultured in a 24-well tissue culture plate in the presence of 20 mg of purified intact (a) or F(ab')$_2$ fragments (■) of anti-BLA-36. An irrelevant murine monoclonal antibody of the same immunoglobulin class IgG$_3$(□) served as negative control. The cells were removed at a 24 hour interval, counted with a hemacytometer, and assessed for viability by trypanblue-dye exclusion.

DETAILED DESCRIPTION OF THE INVENTION

Figure 1:

In the course of the experimental work that has led to the present invention, a developmentally related antigen expressed on the plasma membrane of B lymphocytes and on the surface of Reed-Sternberg cells and Hodgkin's cells was identified using a monoclonal antibody produced by immunization of a BALB/c mouse with a Hodgkin's cell line (HDLM-3F). The antigen with a molecule weight of 36,000 Dalton has been termed B lymphocyte antigen 36 (BLA-36), and its antibody was called anti-BLA-36. The anti-BLA-36 antibody is produced by the monoclonal antibody-producing hybridoma deposited on Sep. 6, 1990 with the American Type Culture Collection, 12301 Parklawn Drive, Rockville, Md. 20852, and given the designation HB 10539. Later experiments, in which BLA-36 was isolated from various B cell lines, Hodgkin's lines and fresh Hodgkin's tissue, indicated that the molecular weight of this antigen was not dependent on its source.

When immunoperoxidase techniques were used, anti-BLA-36 reacted strongly with the Hodgkin's cell line that served as immunogen, and to a lesser degree with pre-B and B cell lines, but showed no detectable binding activity with other hematopoietic cell lines.

In normal tissues, BLA-36 was detectable predominantly on cells in the germinal center and mantle zone of reactive follicles in lymph nodes and spleen. In hematopoietic malignancy, BLA-36 antigen was detectable on the surface of Reed-Sternberg cells, mononuclear Hodgkin's cells, and on malignant cells of B-cell lineage. Under these conditions, T lymphocytes, histiocytes, granulocytes, macrophages, and stromal cells in lymphoid tissue were consistently negative for the expression of the antigen. BLA-36 antigen was not detectable on unactivated (resting) peripheral monocytes, B or T cells and on activated T cells, and was expressed on phorbol diester (PMA)-activated peripheral B cells.

The findings in lymphomas exactly mirrored the patterns of staining observed in the cell line panels that were examined. T-cell lymphomas and diffuse histiocytic lymphomas were consistently nonreactive. B-cell lymphomas (Raji and Daudi) and the so called pre-B cell line (SUAMB-1 and SUAMB-2) were, by contrast, clearly reactive, as were examples of lymphoblastoid and undifferentiated lymphoma (BL-1 and Nu-LB-1), all of which show some features of B-cell differentiation. Furthermore, acute lymphoblastic leukemia of B-cell derivation (BALL-1 and BALM-2) clearly showed positivity with the antibody.

The experimental results indicated that anti-BLA-36, unlike most other antileukocyte antibodies, retained its immunoreactivity in paraffin-embedded tissue sections, and distinguished Reed-Sternberg cells and B-cell lymphomas from all other malignant cells.

BLA-36 also appears to have a role in growth regulation. When antibody to BLA-36 is added to BLA-36 positive cell line (B cell or Hodgkin's disease-derived), growth of the cell line is markedly inhibited. Cell proliferation is halted, and DNA synthesis is markedly reduced. This effect is cytostatic, rather than cytotoxic, and is reversible on removal of the monoclonal antibody from the culture medium. This growth regulatory effect, with inhibition in these conditions, further distinguishes BLA-36 and its corresponding antibody, from other known B cell antigen-antibodies, which do not show inhibitory activity.

The antibody anti-BLA-36 of the present invention may be obtained through conventional monoclonal antibody preparation techniques. Antigen BLA-36 may be separated from cells (tissues) by which it is specifically expressed, through conventional separation techniques. First, the cell membranes are disrupted by freezing and thawing, by mechanical techniques, or by other suitable methods. The soluble cytoplasmic fraction is then separated from the generally insoluble structural elements and nuclei, for example by centrifugation. The antigen may, for example, be isolated by gel electrophoresis, under denaturing conditions.

If the anti-BLA-36 is to be used for diagnostic purposes, the antigen-antibody reaction needs to be visualized. Antigen-antibody reactions can be visualized by a variety a methods known in the art, using markers to label either the antibody or the antigen. At present, the most commonly used markers are chromogens, such as fluorochromes, enzymes, radioactive and radiopaque compounds.

Fluorochromes are dyes that absorb radiation, for example ultraviolet light, are excited by it and as a result, emit visible light. Fluorochromes that are useful as markers must be capable of forming covalent bonds with protein molecules and having a high fluorescence emission in the visible spectrum with a color different from that of tissues. At present, the most commonly used fluorochromes are fluorescein isothiocyanate (FITC) and tetramethyl-rhodamine isothiocyanate (TRITC).

The methods that use antibodies labeled with fluorochrome markers are usually referred to as immunofluorescence methods. In the so called "direct method" fluorochrome-labeled antibody is applied to the preparation containing the corresponding antigen. In the "indirect method" the antigen is treated with its corresponding unlabeled antibody, and the resultant antigen-antibody complex is treated with a fluorochrome-labeled antibody to the immunoglobulin of the animal species that provided the unlabeled antibody used in the first step. In diagnostic immunology, the antigen-containing substrate is incubated with the patient's serum, and then with fluorochrome-labeled mouse, rabbit or goat antibody to human immunoglobulins. The indirect method is usually preferred, due to its higher sensitivity.

For visualizing immunofluorescent specimens, fluorescence microscopes, that are simple modifications of standard transmitted light microscopes, can be used. If necessary, the results may be recorded by photomicrography.

Enzymes may also be used as labels if, on interaction with their substrate, they form a visible well-defined, colored precipitate. Immunoenzyme procedures can be used to localize antigens with the aid of enzyme-labeled antibodies. Several enzymes have been employed as markers, but the most commonly used is horseradish peroxidase, and the methods based upon the use of this enzyme are referred to an immunoperoxidase procedures. Another commonly used enzyme marker is alkaline phosphatase. The most widely used protocol for the detection of antigens by means of enzyme-linked antibodies is referred to as Enzyme Linked Immunosorbent Assay (ELISA) that may be performed as a direct method or in sandwich format.

As radioactive markers, any of the well-known medical radionuclides can be used. Suitable radionuclides include Tc-99m, I-123, In-111, In-113m, Ga-67, or other suitable gamma-emitters.

The radionuclides can be conjugated to the monoclonal antibody of the present invention by conventional techniques. Iodination, for example, mag be accomplished using the chloramine-T method described by S. Mills, et al. $^{123}$I-Radiolabeling of Monoclonal Antibodies for In Vivo Procedures, *Hybridoma* 5, 265–275 (1986). This technique may be used to effect iodination to render the antibody radiopaque, or to attach a radionuclide, such as I-125 or I-131.

Other radionuclides may be attached to the antibody through chelation with benzyl EDTA or DPTA conjugation procedures. Still other suitable techniques include the iodogen method disclosed by M. Pimm, et al., In Vivo Localization of Anti-Osteogenic Sarcoma 791T Monoclonal Antibody, *Int. J. Cancer.* 30, 75 (1982), and direct iodination with radioactive sodium iodide.

Radiopaque materials suitable for labeling antibodies include iodine compounds, barium compounds, gallium compounds, thallium compounds, and the like. Specific examples of radiopaque materials include barium, diatrizoate, ethiodized oil, gallium citrate, iocarmic acid, iocetamic acid, iodamide, iodipamide, iodoxamic acid, iogulamide, iohexol, iopamidol, iopanoic acid, ioprocemic acid, iosefamic acid, acid, iosulamide meglumine, iosumetic acid, iotasul, iotetric acid, iothalamic acid, iotroxic acid, ioxaglic acid, ioxotrizoic acid, ipodate, meglumine, metrizamide, metrizoate, propylidone, and thallous chloride.

In another aspect, the invention relates to methods for imaging lesions characteristic of Hodgkin's disease. For this purpose, the anti-BLA-36 antibody is labeled. Suitable labels includes, for example, radiolabels, radiopaque materials, and magnetic resonance-enhancing materials.

The radiolabels and radiopaque materials have been discussed hereinabove.

Suitable techniques for imaging labels localized in tissues expressing the BLA-36 antibody are known in the art. For example, if the label is a gamma-emitting radionuclide, suitable imaging techniques include gamma cameras and single photon emission computed tomography (SPECT) techniques. If the antibody has been labeled with a radiopaque material, radiographic imaging may be applied. Other suitable techniques include computed axial tomography (CAT) scans, fluoroscopy and conventional X-ray imaging.

Materials that can be detected by or that enhance the effects of magnetic resonance imaging equipment also may be conjugated to the antibodies. Suitable conventional magnetic resonance-enhancing compounds include gadolinium, copper, iron, and chromium. It is preferred that these metal atoms be prepared in the form of conventional organometallic chelates, which are then bound to the antibody.

The foregoing methods along with other routine techniques of immunodiagnosis are disclosed in standard laboratory textbooks. See, for example, Rose, N. R. and Pierluigi, E. B. in Methods in Immunodiagnosis, Second Edition, John Wiley & Sons, Publishers, New York, Chichester, Brisbane, Toronto, 1980; Current Protocols in Molecular Biology, Green Publishing Associates and Wiley-Interscience, 1987.

In a particularly important aspect, the present invention relates to a method for inhibiting the growth of Reed-Sternberg cells, Hodgkin's cells or activated or early proliferating B cells by contacting such cells with a growth-inhibiting amount of anti-BLA-36 antibody or a (Fab')$_2$ fragment thereof. Although the amount of antibody that may be needed for the inhibition of cell growth is a function of the cell type, the extent of undesired cell proliferation, and other conditions, it generally is between about 0.1 and about 1.0 µg/ml.

Further details of the invention are set forth in the following non-limiting Examples.

More specifically, details of the identification and characterization of the BLA-36 cell surface glycoprotein and the anti-BLA-36 antigen are given in Example 1.

Results of a study, exploring the diagnostic utility of anti-BLA-36 by application to a variety of Hodgkin's and non-Hodgkin's lymphomas, in comparison with other antibodies which also react in B5-fixed and paraffin-embedded tissue, are disclosed in Example 2.

EXAMPLE 1

Characterization of a Cell-Surface Molecule Expressed on B Lymphocytes and Hodgkin's Cells A. Materials and Methods Materials. Affinity purified immunoglobulin G fraction of horse antimouse immunoglobulin and avidin-biotin-peroxidase complex (ABC) were purchased from Vector Laboratories, Burlingame, Calif. Reagents for electrophoresis and Western blotting were bought from Bio-Rad Laboratory, Richmond, Calif. Endo-B-N-acetylglucosaminidase H was obtained from Boehringer Mannheim Biochemicals. Pepsin and other chemical reagents were of the highest purity available from Sigma Chemical Co., St. Louis, Mo.

Cell Lines. The Hodgkin's cell line HDLM-3 derived from a malignant pleural effusion in a patient with Hodgkin's disease was provided by Dr. George Moore, University of Colorado, Denver. This and related cell lines HDLM-1 and HDLM-2 have been described elsewhere (6–9). The cell lines utilized in this study are listed in Table 1.

Cell Fusion and Hybrid Selection. Three-weeks old BALB/c mice were immunized with 3 separate injections of $10^7$ HDLM-3 cells/mouse at three-week intervals. The spleen was removed on the 4th day after the last injection and the spleen cells were fused with the mouse myeloma cell line (SP-2) as first described by Kohler and Milstein (10).

Screening, Selection and Cloning of Hybridoma. The initial screening of hybridoma supernatants was performed using cytopreparations of Hodgkin's (HDLM-3), B (Raji) and T (CEM) cell lines. Two hundred thousand cells in 100 µl of medium were used for making each cytopreparation. Cells were fixed for 30 seconds with cold acetone prior to immunocytological staining. Supernatants (100 µl from wells exhibiting hybrid growth were applied and incubated with the cytospin preparation for 30 min. The slides were washed with PBS, and 100 µl of biotinylated horse antimouse immunoglobulin at a predetermined dilution was added to each. After an incubation of 30 min, slides were again washed as above and were incubated with 100 µl of avidin-biotin-horseradish peroxidase complex (ABC) for 30 min. Following a wash with PBS, the bound ABC was visualized by addition of a mixture of the substrate $H_2O_2$, and chromogen, aminoethyl carbazole (AEC).

TABLE 1

Reactivity of Antibody to BLA-36 with Hodgkin's and Hematopoietic Cell Lines by an Indirect Immunocytological Staining Method

| Cell Line | Reactivity with Antibody to BLA-36 | Cell Line | Reactivity with antibody to BLA.36 |
|---|---|---|---|
| Hodgkin's disease: | | Acute lymphoblastic | |
| HDLM-3 | +++ | leukemia: | |
| Burkitt's lymphoma: | | T cell-CEM | − |
| RAJI | + | MOLT-4 | − |
| DAUDI | + | HSB-2 | − |

TABLE 1-continued

Reactivity of Antibody to BLA-36 with Hodgkin's and Hematopoietic Cell Lines by an Indirect Immunocytological Staining Method

| Cell Line | Reactivity with Antibody to BLA-36 | Cell Line | Reactivity with antibody to BLA.36 |
|---|---|---|---|
| SU-AMB-1 | + | HPB-ALL | − |
| SU-AMB-2 | + | JM | − |
| Undifferentiated lymphoma:[b] | | Null cell - NALL - 1 | − |
| | | REH | − |
| NU-DUL-1 | + | B cell - BALL-1 | + |
| U-698-M | + | BALM-2 | + |
| Lymphoblastoid:[b] | | NALM-6 (pre B) | + |
| BL-1 | + | NALM-1 (pre B from CML) | + |
| NU-LB-1 | + | | |
| Large cell lymphoma: | | Myeloid leukemia: | |
| SU-DHL-1 | − | Erythroid - K562 (CML) | |
| -SU-DHL-2 | − | | |
| SU-DHL-4 | − | Myeloid - ML-2 | − |
| U-937 | − | Promyelocytic - HL-60 | − |
| | | Monocytic - TPC-1-0 | − |
| | | Myeloma: | |
| | | IJ-266 | |
| | | ARH-77 | |

NOTE: Sections were scored for intensity on a scale from − to +++: − = abscence of staining; + = weak staining; ++ = moderate staining; +++ = intense staining.
[b]Show evidence of B cell differentiation.

Supernatants containing antibodies with strong reactivity to Hodgkin's cells but none with the T cell lines, were subsequently screened on freshly frozen tissue and on B5-fixed and paraffin-embedded tissue sections of lymph nodes from patients with Hodgkin's disease. All antibodies showing reactivity against the Hodgkin's cell line also reacted with the B cell lines. Differential reactivity with B cells, therefore, could not be used as a selection criterion. Hybrid cells secreting antibodies with reactivity to Hodgkin's cells in tissue were cloned by limiting dilution. Supernatants from wells with single clonal growth were again subjected to the above screening procedures. Clones showing good production of antibody at this stage were subjected to two cycles of recloning before final selection of a clone for subsequent studies.

Purification of Monoclonal Antibody to BLA-36 Anti-BLA-36 was purified by applying the spent-medium containing the antibody to a column packed with Protein A-Sepharose 4B conjugate. The specifically bound material was eluted from the column with 0.1M Glycine-HCl buffer, pH 2.7. Following elution, the antibody was immediately dialyzed with several changes of PBS at 4° C., and was concentrated to yield 1 mg protein per ml in PBS. The purity of the antibody was determined by SDS-polyacrylamide gel electrophoretic analysis. The antibody was characterized as $IgG_3$ subtype. The labelling of the purified antibody with biotin was carried out at room temperature as described previously (11). Subsequently, $F(ab')_2$ fragments of monoclonal antibody to BLA-36 were prepared according to the method of Parham (12). $F(ab')_2$ fragments were then purified on a 2-m-long Sephacryl S-200 column and were assessed for purity by sodium dodecyl sulphate-polyacrylamide gel electrophoresis (SDS-PAGE). Both the whole and $F(ab')_2$ fragments of the antibody were sterilized by filtration before use.

Comparison of BLA-36 With Other Known Antigens of B Cells. Competitive immunoblocking staining assays were performed using immunocytological techniques in order to investigate the nature of the epitopes recognized by anti-BLA-36 in relation to other known antigens of human hematopoietic cells. The cytopreparations of Hodgkin's and B cell lines were incubated first with the unlabelled test antibodies that recognize B cell antigens [(BA-1 (13), BA-2 (14), B-1 (15), B-4 (16), LN-1 and LN-2 (17), anti-mu chain or SC2 antibody to HLA-DR (Table 2)], followed by incubation with biotinylated antibody to BLA-36. The remainder of the staining procedure was as described above. Any change in the intensity of staining with reference to control preparations was recorded.

Preparation and Staining of Tissue Sections. Normal neoplastic and fetal tissues were obtained from the surgical pathology files of the University of Southern California School of Medicine, Los Angeles County Medical Center. The tissues were fixed in formalin or B5, dehydrated, cleared and embedded in paraffin. Tissue sections were cut at five micron thickness for both Hematoxylin and Eosin preparations and immunostaining.

An indirect unlabelled primary antibody method was used for localizing antigen with the specific antibody as described elsewhere (18). Biotinylated horse antimouse immunoglobulin was used as the link between the specific antibody and the ABC. Throughout this study, primary and secondary antibodies and ABC reagent were used at a constant concentration as determined by initial optimal titration analysis. The visual estimates of intensities were scored as follows: −, absence; 1+, weak; 2+, moderate; and 3+, intense. For each experiment, negative controls were performed to ensure the specificity of the reaction: these included the use of specific antibody following absorption with the immunogen (HDLM-3) and an irrelevant antibody of the same immunoglobulin class in lieu of the specific antibody.

Preparation of Cell Lysate. The cell lines ($10^7$ cell/ml) were washed three times in serum-free medium. The cells were lysed with 20 mM Tris HCl buffer, pH 7.5, containing 0.5% (v/v) noidet P-40 (NP-40), 1.0 mM phenylmethylsulphonyl fluoride and 0.5 mM chloromethyl-L-(2-phenyl-1-toluenesulphoamido) ethyl ketone (lysis buffer). Lysates were incubated on ice for 15 min and clarified by centrifugation at 100,000× g and 4° C. for 15 min. The supernatant was used immediately or stored at −70° C. until further use.

TABLE 2

Comparison of Epitopes Detected by Anti-BLA-36 and Other Known Antibodies to Human Leukocyte Antigens by an Immunocytochemical Steric Inference (Blocking) Assay

| Initial Incubation[a] | Second Incubation | Immunoperoxidase labelling | Intensity of staining[b] |
|---|---|---|---|
| PBS | Biotinylated anti-BLA-36 | ABC | +++ |
| anti-BLA-36 | Biotinylated anti-BLA-36 | ABC | − |

TABLE 2-continued

Comparison of Epitopes Detected by Anti-BLA-36 and Other Known Antibodies to Human Leukocyte Antigens by an Immunocytochemical Steric Inference (Blocking) Assay

| Initial Incubation[a] | Second Incubation | Immuno-peroxidase labelling | Intensity of staining[b] |
|---|---|---|---|
| anti-BA-1 | Biotinylated anti-BLA-36 | ABC | +++ |
| anti-BA-2 | Biotinylated anti-BLA-36 | ABC | +++ |
| anti-B-1 | Biotinylated anti-BLA-36 | ABC | +++ |
| anti-B-4 | Biotinylated anti-BLA-36 | ABC | +++ |
| LN-1 | Biotinylated anti-BLA-36 | ABC | +++ |
| LN-2 | Biotinylated anti-BLA-36 | ABC | +++ |
| anti-mu chain | Biotinylated anti-BLA-36 | ABC | +++ |
| SC-2 | Biotinylated anti-BLA-36 | ABC | +++ |

[a]Positive controls to demonstrate effective binding of anti-BA-2, anti-B1, anti-B4, anti-mu chain and SC2 monoclonal antibodies were performed using the indirect immunoperoxidase method and the appropriate cell lines (HDLM-3, DAUDI and RAJI) and confirm that each of these antibodies bound to target cells.
[b]Mean value for three cell lines (HDLM-3, RAJI, and DAUDI) utilized in this study.

Western Blot Analysis. Following separation of the NP-40 solubilized material from Hodgkin's tissue, from BLA-36-positive cell lines (Hodgkin's, pre-B or B cell) and BLA-36-negative cell lines (T and Null cell acute lymphoblastic leukemia, myeloid leukemia) by sodium dodecyl sulphate-polyacrylamide gel electrophoresis (19), the bands were electrophoretically transferred to nitrocellulose filter paper as described by Towbin, et al. (20). Each lane was cut from the filter paper incubated with PBS containing 1% (w/v) gelatin for 1 hour to block the nonspecific binding of antibody to filter paper. Each strip of filter paper was incubated for 30 min with 10 ml of PBS and 100 µl of spent medium containing anti-BLA-36 (10 µg/ml), anti-BLA-36 (10 µg/ml) absorbed with the lysate of HDLM-3 cell line (1 mg/ml), or an equivalent amount of an irrelevant IgG$_3$ antibody that recognizes a glycoprotein on the surface of human breast epithelium. Following incubation, the strips were washed thoroughly with PBS containing 0.05% (v/v) Tween 20 and incubated with horseradish peroxidase conjugated goat antimouse immunoglobulin in an appropriate dilution for 30 min. The strips were once again washed as above. Finally, the color was developed by incubating the strip with PBS containing 1 mM diaminobenzidine and 0.01% hydrogen peroxide for 5 min.

Competitive Western immunoblot analyses were performed to ascertain the nature of antigen recognized by anti-BLA-36 in relation to other closely related antigens, such as the one recognized by LN2 (CD75). Prior to application of the NP-40 solubilized extract of Raji cell line on SDS-PAGE, the samples were first preabsorbed with antibody to BLA-36 or CD75, immobilized individually to Sepharose 4B as described previously (21). Each antibody (5 mg/ml of Sepharose 4B suspension) was separately mixed and incubated with the Raji extract (1mg protein/ml). Following an overnight incubation, the suspension was centrifuged at 10,000× g and 4° C. for 15 min. The supernatant containing the preabsorbed extract was removed and subsequently analyzed by Western immunoblot method. Following the application of the unabsorbed or absorbed extracts on SDS-PAGE, the protein bands were electrophoretically transferred to nitrocellulose filter-paper and then each strip of the filter-paper was allowed to react with the appropriate antibody. The negative control consisted of strip containing the extract which was preabsorbed with the antibody that also subsequently served as a reacting antibody.

Determination of epitope recognized by anti-BLA-36. Studies were conducted to determine whether the antibody was directed to a protein and/or the carbohydrate antigen as described below. Protein (250 µl) from NP-40-solubilized extract of HDLM-3 was incubated at 37° C. for 18 hours in 100 µl of 0.1M sodium citrate buffer, pH 5.5, containing 50 milliunits of endo-β-N-acetylglucosaminidase H as described by Tarentino, et al. (22). Following incubation, the reaction mixture was mixed with an equal volume of cold 12.5% (w/v) trichloracetic acid (TCA) for 15 min at 4° C. The mixture was centrifuged at 12,000× g for 15 min, and the supernatant was removed and dialyzed against several changes of PBS at 4° C. The pellet was dissolved in 100 µl of PBS and dialyzed. To ensure complete precipitation, a control containing only the protein in the absence of the enzyme was included. Protein (250µ) from NP-40-solubilized extract of HDLM-3 was dissolved in 100 µl of 0.07M sodium acetate buffer, pH 4.0, containing 0.05M Nacl and 15 µg of pepsin, and the reaction mixture was incubated at 37° C. in a water-bath for 18 hours. At the end of the enzyme-digestion period, the pH of the solution was adjusted to 8 with NaOH and was dialyzed against several changes of PBS.

Effect of the Growth of Hodgkin's Cell Line. Hodgkin's, B, T, and histiocytic lymphoma cell lines were cultured in triplicate (1.8×10⁵ cells/ml) in serum-free defined medium (HB 101, Hana Biologics, Alameda, Calif.) in 24-well tissue culture plates. Cells were cultured in the presence of various concentrations ranging from 0.12 to 4.0 µg of intact or F(ab')$_2$ fragments of (a) specific antibody, or (b) equivalent amounts of specific antibody preabsorbed with the extract of HDLM-3 or (c) an irrelevant control antibody of the same immunoglobulin class, in order to assess the effect of anti-BLA-36 on cellular proliferation. BLA-36-negative hematopoietic cell lines also served as negative controls. The cells in each well were incubated for various lengths of time and their numbers were counted by hemacytometer on day 4 (for the titration of antibody) or at intervals of 24 hrs. for 5 days. The viability of cells was determined by trypan-blue-dye exclusion limit.

B. Results

Generation, Cloning and Screening of Monoclonal Antibodies. Supernatants from wells exhibiting hybridoma growth were screened by immunocytochemical staining of cytopreparations of a Hodgkin's (HDLM-3), a B (Raji) and a T (CEM) cell line. Supernatants with no reactivity or with reactivity against all three cell lines were rejected. A small number of supernatants lacked reactivity against the T cell lines, but showed strong positivity with Hodgkin's cells and B cells. Supernatants with reactivity against the Hodgkin's cell line alone were not detected. Those hybrids producing antibodies with strong reactivity to Hodgkin's cell line, but not to T cells were repeatedly subcloned, until one clone, producing consistently high levels of monoclonal antibody with the above properties, was selected for detailed study. Double immunodiffusion studies with goat antibodies to subclass of mouse immunoglobulin revealed that anti-BLA-36 is an IgG$_3$ immunoglobulin. The primary parameter for selection of anti-BLA-36 was its ability to react strongly with its antigen both in a Hodgkin's related cell line and tissue sections. The screening process also revealed that the epitope recognized by anti-BLA-36 is resistant to B5- or formalin-fixation and paraffin-embedding procedures.

Immunocytologic Localization of Antigen in Cell Lines. In order to test the specific expression of the target antigen, several cell lines of human hematopoietic lineage were incorporated in an indirect immunoperoxidase staining technique. The Hodgkin's cell line and also pre-B and B cell lines included in the assay showed reactivity with the antibody. Anti-BLA-36 showed strong binding reactivity predominantly with the surface membrane and to a lesser extent with the cytoplasm of the Hodgkin's cell line (Figure). There was no detectable binding reactivity with non-B hematopoietic cell lines, including those of T cell, myeloid, and monocyte origin, suggesting that the antigen concerned is expressed on Hodgkin's and B cell lines only (Table 1). Absorption of specific antibody with the immunogen led to a complete abolition of staining of the Hodgkin's cells. Also, negative controls in which anti-BLA-36 was replaced by an irrelevant antibody of the same immunoglobulin class showed no reactivity.

Comparisons of Epitope Recognized by Anti-BLA-36 with Other Known and Characterized Lymphoid Antigens. The expression of antigen recognized by anti-BLA-36 was compared with other well characterized hematopoietic antigens to which commercial antibodies are available. Anti-BLA-36 showed strong reactivity with the Hodgkin's cell line and also with B and pre-B cell lines and no reactivity with large cell lymphoma or T cells lines. Antibody B-1 failed to react with the Hodgkin's cell line while antibodies BA-2 and B-4 showed weak reactivity. Conversely, antibodies to. T cells (Leu4) or granulocytes/monocytes (OKM1 and LeuM1) showed no evidence of binding reactivity with Hodgkin's line. Furthermore, preadsorption of B cell antibodies BA-1, BA-2, B-1, B-4, LN-1, LN-2, IgM (mu chain) and HLA-DR (SC2) to the Hodgkin's cell line showed no reduction staining when the Hodgkin's cell line was subsequently treated with biotinylated anti-BLA-36. The result suggests that the epitope recognized by anti-BLA-36 is distinct from those recognized by other antibodies studied (Table 2).

Immunohistological Localization of Antigen in Tissue Section. The specificity and pattern of anti-BLA-36 was further studied in fresh-frozen and B5-fixed and paraffin-embedded tissue sections using an indirect avidin-biotin peroxidase complex (ABC) method.

Initially, the antibody was reacted with frozen tissue sections of normal lymph nodes and spleen, in addition to lymph nodes from patients with Hodgkin's disease. In later studies, formalin or B5-fixed and paraffin-embedded tissue sections were employed. The pattern of reactivity of anti-BLA-36 was identical in frozen and formalin or B-5-paraffin sections, leading to a preference for the latter based on superior morphology.

Figure 2A:
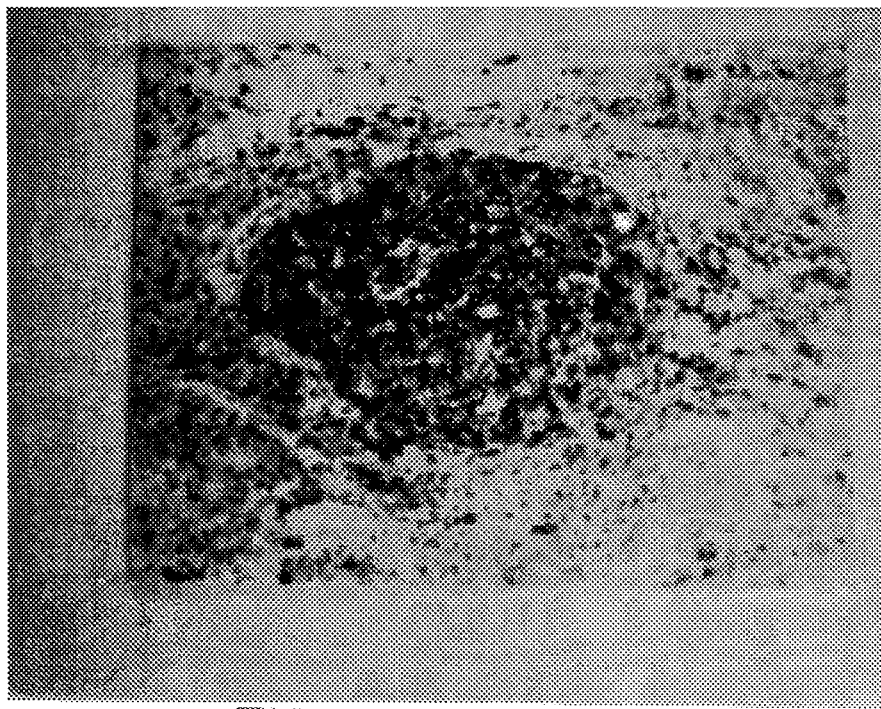

Anti-BLA-36 showed strong reactivity to a subset of lymphocytes in the follicle and mantle zone of normal lymph nodes (FIG. 2a). The percentage of cells showing reactivity in mantle and within the follicle was 70 to 80 and 100% respectively, encompassing both small and large cells. BLA-36 was predominantly localized on the cell-surface. The specificity and patterns of reactivity of the antibody in normal spleen were similar to those obtained with lymph node. Under these conditions, the tangible body macrophages, dendritic reticulum cells, interdigitating reticulum cells, sinus histiocytes and endothelial cells were consistently negative, as were presumptive T lymphocytes in the paracortex (Table 3).

TABLE 3

Reactivity of Antibody to BLA-36 with Hematopoietic Cells in Freshly Frozen or B5-Fixed Paraffin-Embedded Sections

| Tissue | Reactivity with Antibody to BLA-36 |
|---|---|
| Lymph node: | |
| Germinal center | +++ |
| Mantle zone | +++ |
| T cell zone | − |
| Interdigitating histiocyte | − |
| Sinus histiocyte | − |
| Endothelium | − |
| Spleen: | |
| White pulp | +++ |
| Red pulp | − |

Figure 2B:
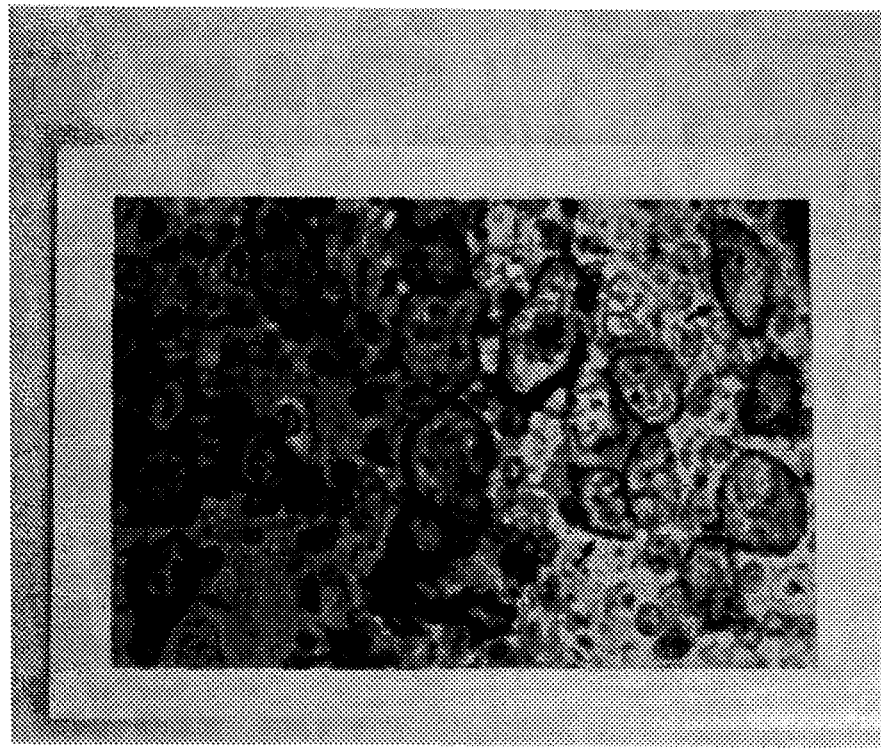

Anti-BLA-36 also showed strong reactivity with Reed-Sternberg cells and their variants in lymph nodes of patients with Hodgkin's disease. The reactivity was predominantly on the plasma membrane (FIG. 2b), but with definite cytoplasmic staining visible in the Golgi area of larger Reed-Sternberg cells. A high proportion (90%) of Reed-Sternberg cells showed intense staining (Table 4). Scattered small lymphocytes present in lymph nodes involved by Hodgkin's disease also showed reactivity, especially where residual follicles were identifiable. The Reed-Sternberg cells and mononuclear Hodgkin's cells were positive in all 28 cases of Hodgkin's disease that were studied.

Subsequently, 31 cases of non-Hodgkin's lymphomas were examined. The antibody showed strong reactivity with B cell lymphomas (Table 5), including follicular center cell lymphomas (large and small cell types), mantle zone (also known as intermediate cell) lymphomas, and immunoblastic sarcomas. The T cell lymphomas and chronic lymphocytic leukemia (CLL) consistently showed no reactivity (Table 5).

Under identical condition, anti-BLA-36 showed no reactivity with normal epithelial cells, including adrenal gland, breast, colon, lung, salivary gland, skin and stomach and their malignant counterparts. A variable proportion of Kupffer cells in normal liver, however, showed weak reactivity with the antibody. Connective tissue elements were otherwise nonreactive, with the exception of scattered lymphocytes presumed to be B cells.

Characterization of Epitope Recognized by Anti-BLA-36. The immunoreactivity of anti-BLA-36 was abolished by its absorption with TCA-soluble fraction obtained by eno-b-N-acetyglucosaminidase H treatment of the Hodgkin's cell line (Table 6). Absorption with the TCA-precipitable fractions of the endoglycosidase-treated or pepsin-treated cell extracts has no effect on the intensity of the immunostaining. The results are consistent with the thesis that the antibody recognizes an epitope expressed in the carbohydrate domain of a glycoprotein.

TABLE 4

Immunohistological Distribution of BLA-36 Detected by a Xenogeneic Monoclonal Antibody in B5-Fixed Paraffin-Embedded Tissue Sections from Patients with Hodgkin's Disease

| Histology | Total no. of cases | No. Positive | Reed-Sternberg cells and variants (% cells staining) | Intensity of staining |
|---|---|---|---|---|
| Nodular sclerosis | 12 | 12 | 85–95 | +++ |
| Mixed cellularity | 9 | 9 | 75–90 | +++ |
| Lymphocyte depleted | 3 | 3 | 75–90 | +++ |

TABLE 4-continued

Immunohistological Distribution of BLA-36 Detected by
a Xenogeneic Monoclonal Antibody in B5-Fixed Paraffin-Embedded
Tissue Sections from Patients with Hodgkin's Disease

| Histology | Total no. of cases | No. Positive | Reed-Sternberg cells and variants (% cells staining) | Intensity of staining |
|---|---|---|---|---|
| Lymphocyte predominant | 4 | 4 | 75–90 | +++ |

TABLE 5

Immunohistological Distribution of BLA-36 Detected by
a Xenogeneic Monoclonal Antibody in B5-Fixed Paraffin-Embedded
Tissue Sections from Patients with Hematopoietic Malignant Diseases
(Other Than Hodgkin's Disease)

| Histology | Total no. of cases | No. positive | Intensity % of cells staining | Intensity of staining |
|---|---|---|---|---|
| B-immunoblastic sarcoma | 7 | 7 | 70–90 | +++ |
| T-immunoblastic sarcoma | 6 | 0 | 0 | − |
| Follicular center cell (large) lymphoma[a] | 8 | 8 | 75–85 | ++ |
| Follicular center cell (small cleaved) lymphoma[b] | 3 | 3 | 80 | +++ |
| Follicular center cell (small non-cleaved) lymphoma | 3 | 3 | 80 | +++ |
| Mantle zone lymphoma | 2 | 2 | 80 | +++ |
| Chronic lymphocytic | 2 | 0 | 0 | − |

[a]Combines large cleaved and large non-cleaved types.
[b]Large cell component, small cells showed weak reactivity.

TABLE 6

Determination of the Nature of Epitope Recognized by
Monoclonal Antibody to BLA-36

| Treatment of HDLM.3 extract | Binding properties of antibody to BLA-36 bsorbed with treated extract of HDLM.3 cells to cellular antigen in tissue sections |
|---|---|
| (a) Endo-β-N-acetylglucosaminidase H | Reactive (TCA-precipitable fraction) Non-reactive (TCA-soluble fraction |
| (b) Pepsin | Reactive |

Anti-BLA-36 antibody was absorbed with the extract of Hodgkin's cell line (HLDM.3) treated with (a) Trichloroacetic acid (TCA) - precipitable and -soluble fractions resulting from endo-β-N-acetylglucosaminidase; and (b) pepsin as described in the text.

Figure 3:
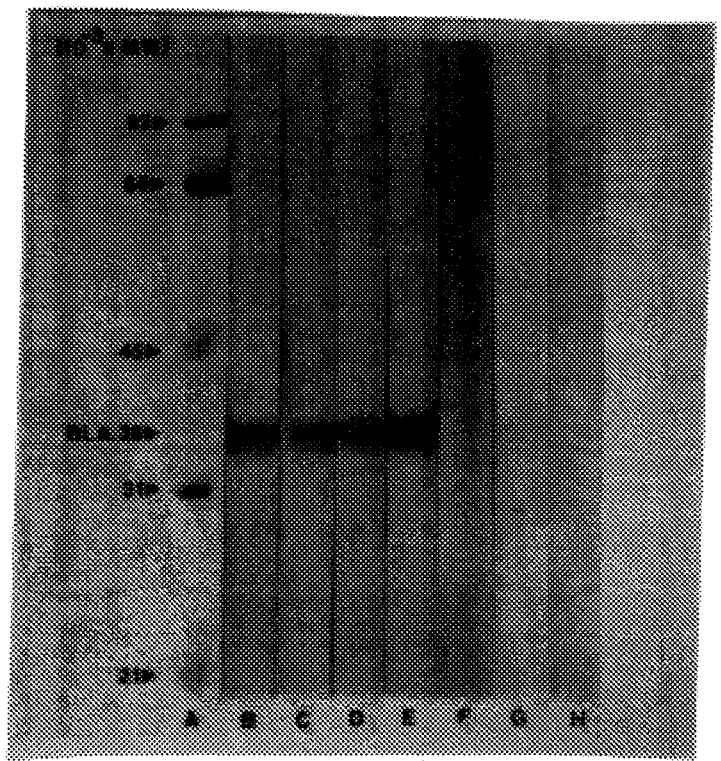

Characterization and Comparison of BLA-36 with Other Known Lymphoid Antigen. Antigen specifically recognized by anti-BLA-36 was analyzed by Western-immunoblotting method. Western-immuno-blot analysis of non-reduced extracts (NP-40 solubilized) of the Hodgkin's, B and pre-B cell lines and lymph node from a patient with Hodgkin's disease, when reacted with the monoclonal antibody, yielded an antigen with an apparent molecular weight of 36 kilodaltons (FIG. 3, Lanes B–E). Chemical reduction of the cell extract before electrophoresis had no effect on the migration of the antigen (result not illustrated). The use of the extracts of histiocytic and T cell lines in the above experiment failed to yield the antigen (FIG. 3, Lanes F, G) complementing the results obtained in the immunocytological staining of these cells with anti-BLA-36 (Table 1). Furthermore, application of anti-BLA-36 preabsorbed with an extract of BLA-36-positive cell line also showed no reactivity with its corresponding band on the strip (FIG. 3, Lane H).

Figure 4:
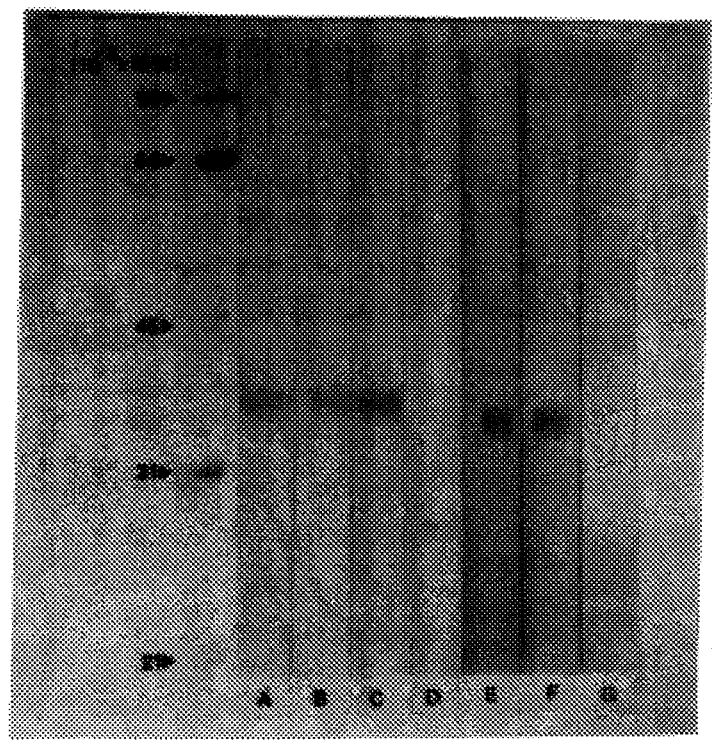

Finally, BLA-36 was compared with other known lymphoid antigens by Western-immunoblot method. Owing to a weak reactivity of LN2 (CD75) with HDLM-3 cell line, the NP-40 solubilized extract of a B cell line (Raji) was used as a source of target antigens for the both antibodies included in this experiment. The anti-BLA-36 and CD75 showed a strong reactivity with their corresponding antigens with the apparent molecular weights of 36 and 35 kilodaltons respectively (FIG. 4, Lanes A and E). The application of anti-BLA-36 on the strip of filter-paper containing the extract of Raji cell line (FIG. 4, Lane B) or Hodgkin's disease tissue (FIG. 4, Lane C), which were preabsorbed with immobilized LN2 antibody, exhibited a band corresponding to BLA-36. Likewise, preabsorption of the extract with the immobilized anti-BLA-36 showed no effect on the antigen recognized by LN2 antibody (FIG. 4, Lane F). The strip containing extract which was preabsorbed and subsequently incubated with the same antibody led to the abolition of the reactivity, attesting to the specificity of reaction and the effectiveness of the absorption procedure (FIG. 4, Lanes D and G).

Figure 5:
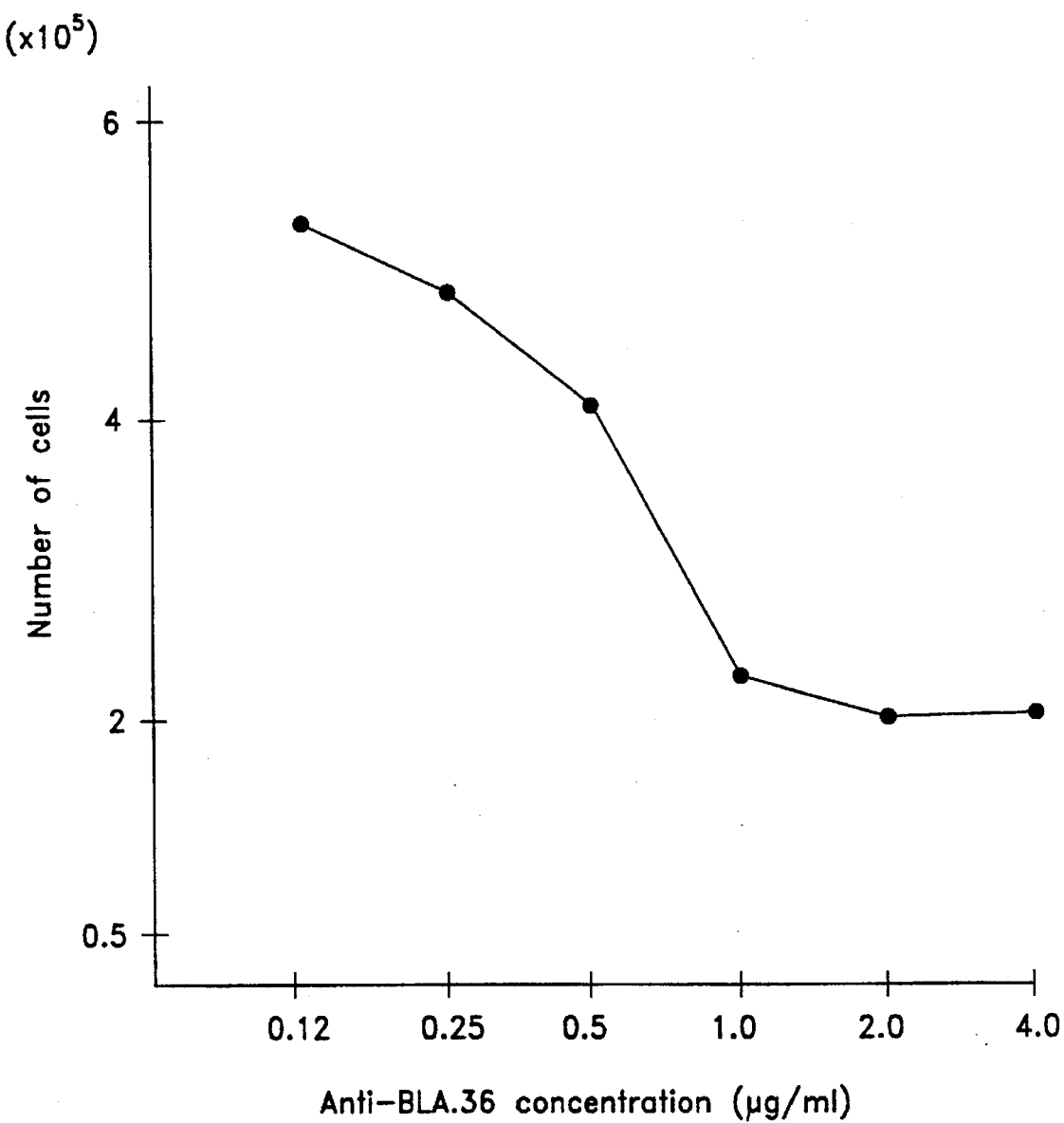

Effect of Anti-BLA-36 on Cell-Growth. In order to explore the effect of anti-BLA-36 on cell growth, Hodgkin's B, T, and large cell lymphoma cell lines were grown for 4 days in the presence of various concentration ranging from 0.12 to 4.0 μg of intact or F(ab')$_2$ fragments of the antibody. The antibody concentrations in the range of 1 to 2 μg/ml completely inhibited the growth of the Hodgkin's cell line (FIG. 5) and B cell lines (results not shown). The inhibition of growth of the Hodgkin's cells by the intact antibody to BLA-36 gave a similar titration curve to that shown in FIG. 5. The wells that received either preabsorbed antibody to BLA-36 or an irrelevant monoclonal antibody of the same immunoglobulin class in the above concentrations range showed no inhibition of growth under the same conditions. The number of cells (approximately $0.61 \times 10^5$ cells per well) in the above wells were comparable to those that received medium alone at the end of 4 day incubation period.

Figure 6:
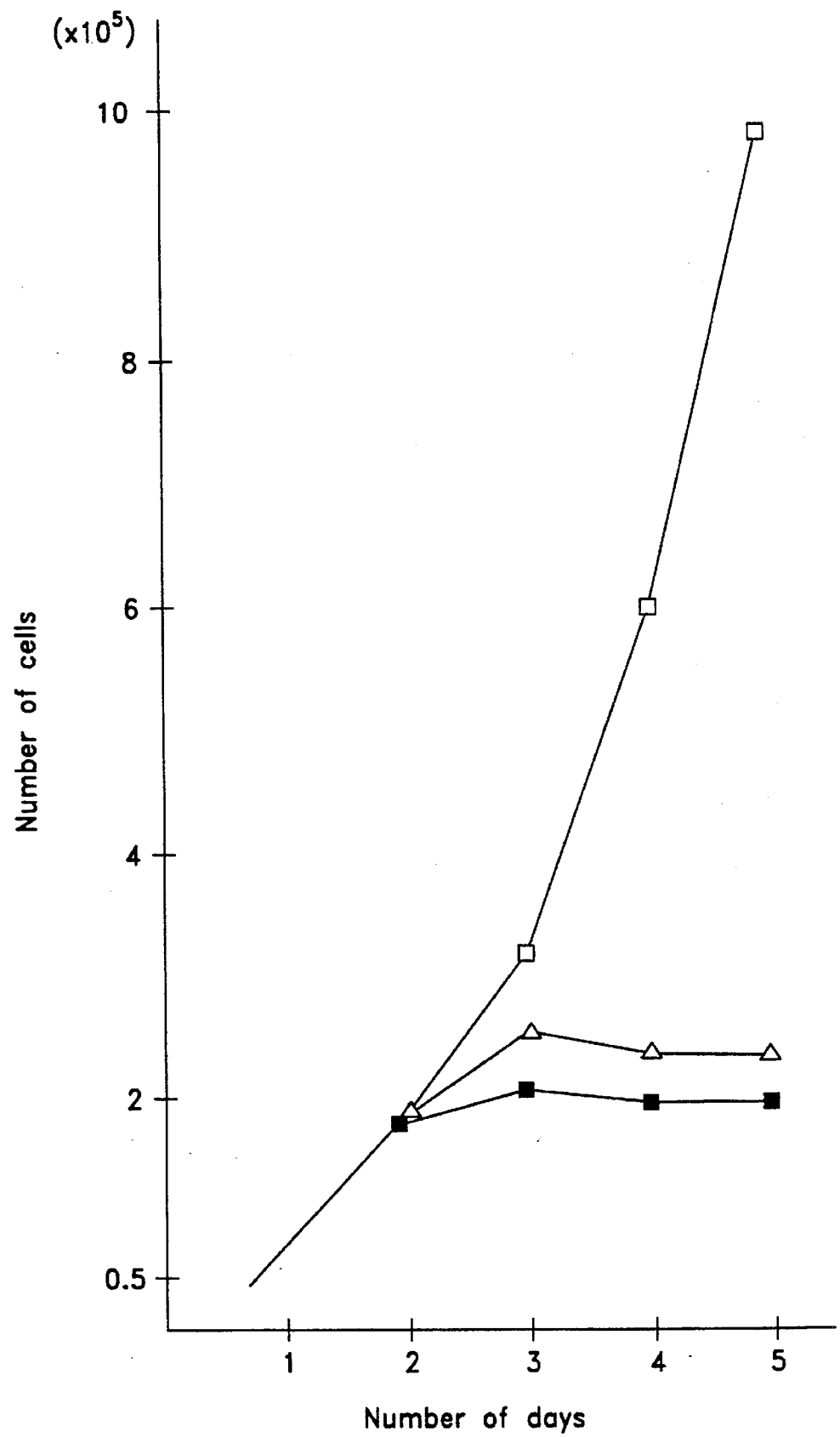

Subsequently, Hodgkin's cell line was grown in the presence of the optimum concentration (2 μg) of intact or F(ab')$_2$ fragments of anti-BLAT36. Following the incubation period, the number of cells in each well was counted by hemacytometer and their viability was determined by trypan-blue-dye exclusion limit at intervals of 24 hrs. for 5 days (FIG. 6). The viability of cells in each well was approximately 98% as determined by the dye-exclusion limit, suggesting that the growth-inhibitory effect of the antibody was cytostatic. Furthermore, such growth-inhibitory effect of anti-BLA-36 was reversed following the removal of the antibody from the culture medium (results not shown). The inhibition of growth was not mediated by the Fc portion of the antibody, since F(ab')$_2$ fragments were as effective as the whole antibody (FIG. 6). An irrelevant monoclonal antibody of the same immunoglobulin class in the above concentration range exhibited no inhibition of growth under the same conditions (FIG. 6). In addition, anti-BLA-36 pre-absorbed with an extract of BLA-36-positive cell line (HDLM-3 or RAJI) exhibited no inhibition of growth under the same condition (results not shown). No growth-inhibitory effect was observed when the antibody in the above concentration range was incubated with antigen negative cell lines (CEM, MOLT-4, U-937, and SU-DUL-1) (results not shown).

C. Discussion

The goal of the present study was to develop monoclonal antibodies with specificity Reed-Sternberg cells, which retained their immunoreactivity in tissues that have been routinely-fixed and embedded in paraffin. It was anticipated that such antibodies might have value in the diagnosis of Hodgkin's diseases, and by their pattern of reactivity, also shed light on the cellular origin of the malignant cell of Hodgkin's disease. Furthermore, with the availability of such antibodies, attempts might be made to characterize and isolate the antigens involved, as a preliminary to determining their functional role. In order to achieve this goal, monoclonal antibodies generated by immunization of mice with HDLM-3, a presumptive Reed-Sternberg or Hodgkin cell line derived from a patient with Hodgkin's disease (9), were screened in a system that required reactivity with Reed-Sternberg cells in fixed paraffin embedded tissues as a selection criterion. Initial screening was performed against the immunogen (HDLM-3, Hodgkin's cell line) using an indirect immunoperoxidase method. Simultaneously, cryopreparations from known B and T cell lines were included in the screening procedure. The initial goal was to discover the presence of antibodies specific to the Hodgkin's cell line with no evidence of reactivity against B or T cells. In these studies, several supernatants containing antibody were identified that reacted with HDLM-3, and not with the T cell line, but all of these showed some reactivity against the B cell lines. These' supernatants were subjected to further screening against a broader panel of cell lines of B, T, or histiocytic type. On this basis, the antibody, eventually designated anti-BLA-36, was selected for further studies. It showed strong reactivity with the cell surface membrane of Reed-Sternberg and Hodgkin's cells in cytopreparations, and frozen or paraffin sections. A less intense reactivity with pre-B and B cell lines and a subset of normal B lymphocytes in tissue was also observed. A variety of other hematopoietic cell lines were uniformly nonreactive, attesting to the specificity of anti-BLA-36 for Reed-Sternberg cells and a subset of B cells.

Competitive experiments were performed to determine whether the reactivity of anti-BLA-36 differed significantly from other anti-leukocyte monoclonal antibodies which are commercially available or described in the literature. These findings are summarized in Table 2 and FIG. 4. Taken in conjunction with specificity and molecular weight data these clearly distinguish anti-BLA-36 from all of the following antibodies that recognize B cell related antigens [LN-1 and LN-2 (17), B-1 (14), B-2 (29), B-4 (15), BVA-1'(13), BA-2 (13), BL-2 (30), B532 (31,32), CB-2 (32), BB-01 (33), B-LAST-1 (34), K19 (35), FMC series (36), GB series (37), OKB series (38), anti Y29-55 (39), BLA (40) and PCA-1 and 2 (41)]. In addition, the KI-1 antibody that recognizes Reed-Sternberg cells and has shown reactivity with certain of the large cell non-Hodgkin's lymphomas, shows no reaction with normal B cells and is clearly distinct, while Leu-M1 differs in being reactive with histiocytes rather than B cells (42). Although the tissue-distribution of BLA-36 is different from B7/BB-1 (43,44), the molecular size of BLA-36 is similar to B7-BB-1. In contrast to BLA-36, CD is not known to be N-glycosylated. Finally, the binding activity of antibody to CD20 with Reed-Sternberg cells has not been reported and was also not detectable in HDLM-3 cell line in this study.

In tissue from patients with Hodgkin's disease, anti-BLA-36 showed evidence of reactivity with Reed-Sternberg cells and mononuclear Hodgkin's cells in frozen and paraffin-embedded tissue sections from all subtypes of Hodgkin's disease. Reactivity was predominantly associated with the plasma membrane, but some of the larger Reed-Sternberg cells showed focal reactivity in a paranuclear compartment, consistent with the location of the Golgi apparatus. The percentage of cells showing positive reactions varied from 75% to almost 100% (Table 4). Of the other cell types identified with lymph nodes involved by Hodgkin's disease, none showed evidence of reactivity, with the exception of scattered B cells in areas where there appeared to be residual follicles with identifiable mantle zones. This pattern of reactivity therefore resembled that observed in normal lymphoid tissue where anti-BLA-36 gave distinctive reactivity within the mantle zone and within the follicle proper. Presumptive T lymphocytes in the paracortex were nonreactive as were other cell types.

When applied to non-Hodgkin's lymphomas, anti-BLA-36 showed reactivity with B cell lymphomas, particularly large cell follicular center cell lymphomas and immunoblastic sarcomas. Mantle zone lymphomas also showed a high proportion of positive cells. T cell lymphomas showed no evidence of reactivity and a wide variety of carcinomas and melanomas tested also were non-reactive. Anti-BLA-36 may, therefore, be of value in immunohistologic studies for distinguishing Hodgkin's disease from this latter group of conditions metastatic to lymph node. It is likely to be less helpful in distinguishing the cellular forms of Hodgkin's disease, or lymphocyte depleted Hodgkin's disease from the large cell lymphomas of B lymphocytic origin. In the present study, the intense reactivity observed with Reed-Sternberg and mononuclear Hodgkin's cells was clearly of value in recognizing these cells when they occurred in small numbers in lymphoid tissues.

The findings in lymphomas exactly mirrored the patterns of staining observed in the cell line panels that were examined. T cell lymphomas, diffuse histiocytic lymphomas, and carcinomas were consistently nonreactive. Burkitt's lymphomas (Raji, Dandi, SU-AMB-1, SU-AMVB-2) were by contrast clearly reactive, as were examples of lymphoblastoid (BL-1, NU-LB-1), and undifferentiated lymphomas (NU-DUL-1, U-698-M), all of which show some features of B cell differentiation. Furthermore, acute lymphoblastic leukemia cell lines of B cell derivation (BALL-1 and BALM-2) clearly showed positivity with the antibody. The results suggest that anti-BLA.26, unlike most other anti-leukocyte antibodies, retains its immunoreactivity in paraffin-embedded tissues sections, and it distinguishes Reed-Sternberg cells and B cell lymphomas from all other malignant cells. Therefore, anti-BLA-36 appears to have diagnostic utility.

Finally, the demonstration that anti-BLA-36 has growth-inhibitory effects in a dose-dependent manner on the antigen positive cell lines suggests a possible growth-regulatory function of BLA-36. The inhibition of growth was not mediated by the Fc portion of the antibody, since F(ab')$_2$ fragments were as effective as the whole antibody. Preliminary studies suggest that the expression of BLA-36 may subserve a receptor function in the sense that it mediates the transmission of signals facilitating proliferation of cells. These aspects are the subject of continuing study.

EXAMPLE 2

Diagnostic Use of Anti-BLA-36 Antibody

A. Materials and Methods

Tissue Sections

Cases with the diagnosis of Hodgkin's disease or non-Hodgkin's lymphoma were obtained from the files of the Hematopathology Division of the Department of Pathology at the Los Angeles County-University of Southern California Medical Center and from the consultation files of the inventors. Cases from the Medical Center were fixed in B5 solution. In the cases obtained from consultation files, the types of fixation could not be determined with certainty in every case.

Cases of Hodgkin's disease were classified according to the Rye Modification of the Lukes-Butler classification (55). Non-Hodgkin's lymphomas were arranged according to the Working Formulation of Non-Hodgkin's Lymphomas (56).

Tissue sections from B5-fixed, paraffin-embedded blocks were cut at 6 microns for hematoxylin and eosin staining and immunohistologic studies.

Immunohistological Staining

Monoclonal antibodies used in this study included anti-BLA-36 (49,50), L26 (51,52), IN-1 (CDW75) (17,47,53), LeuM1 (CD15) (14,53,23), Ber-H2 (CD30) (48,53), and UCHL-1 (CD45RO) (54). An indirect unlabelled primary antibody method (ABC) was used for localizing antigen with the specific antibody as described elsewhere (46,50). All primary antibodies were used at optimum dilutions determined in preliminary studies of cases showing positive or negative reactivity for the respective antigens. Antibody incubations were for 30 minutes at ambient temperature (25°–30° C.). Biotinylated horse anti-mouse immunoglobulin antibody was used in the linking reagent in an ABC conjugate method (reagents from Vector, Burlingame, Calif.). Amino ethyl carbazole was used as the chromogen (46). Visual estimates of intensity of immunostains were evaluated independently by three of the authors (DRD, RKB, and CRT) and were scored as: 0=absent; +=weak; ++=moderate; +++=strong. Table 1 reflects a positive result in cases where the consensus score was at least in the + category for 20% or more of the critical cells under evaluation. For each stain, negative controls were performed to insure the specificity of the reaction. For anti-BLA-36 this also included use of the antibody absorbed with immunogen (cell line HDLM-3), and an irrelevant antibody of the same immunoglobulin class in lieu of the specific antibody. In addition, the stains were performed in large batches of 42–60 slides such that the different cases served as positive and negative controls, each against the others. Finally, for most of the antibodies, individual tissue sections from most cases contained at least some cells reactive with the antibody under evaluation; these cells served as internal positive controls attesting to the validity of the staining procedure (eg, residual B cells for BLA-36, L26; residual T cells for UCHL-1).

Twenty-four cases of non-Hodgkin's lymphomas of B-lymphocyte origin were evaluated. Thirteen of these were characterized at the time of initial diagnosis by immunophenotyping using cryostat-sectioned frozen tissue and B5-fixed tissue. The remaining eleven cases were immunophenotyped prior to use in this study using B5-fixed tissue alone. Four of these had distinct follicular patterns providing further presumptive sarcomas (BIBS) with monoclonal intracellular immunoglobulin; two were mantle zone lymphomas; one was diffuse small non-cleaved, one diffuse large non-cleaved, and the last was a case morphologically typical of BIBS, but in which monoclonal immunoglobulin was not demonstrable.

Sixteen cases of Hodgkin's disease were examined including three cases of lymphocyte predominant, six cases of nodular sclerosis, five cases of mixed cellularity, and two cases of lymphocyte depletion. Frozen section immunohistochemistry had been performed in five of these cases; the findings were consistent with the diagnosis of Hodgkin's disease.

Frozen Tissue

Twenty cases in this study were evaluated using both frozen and B5-fixed tissue. This included five cases of Hodgkin's disease, 13 cases of non-Hodgkin's lymphoma of B-lymphocyte origin, and two non-Hodgkin's lymphomas of T-lymphocyte origin.

B. Results

Hodgkin's Disease

Anti-BLA-36

Figure 7:
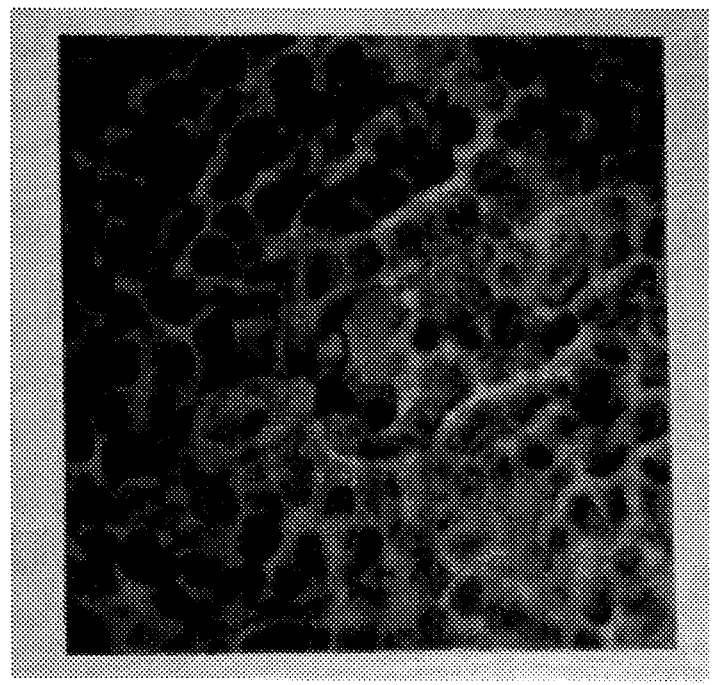
FIG. 7 illustrates a lymphocyte predominant Hodgkin's disease stained with anti-BLA-36 by the immunoperoxidase method. Two L&H variant Reed-Sternberg cells show positive membrane staining (B5 paraffin section; chromogen amino ethyl carbazole (AEC); counterstain hematoxylin; magnification ×500).
Figure 8:
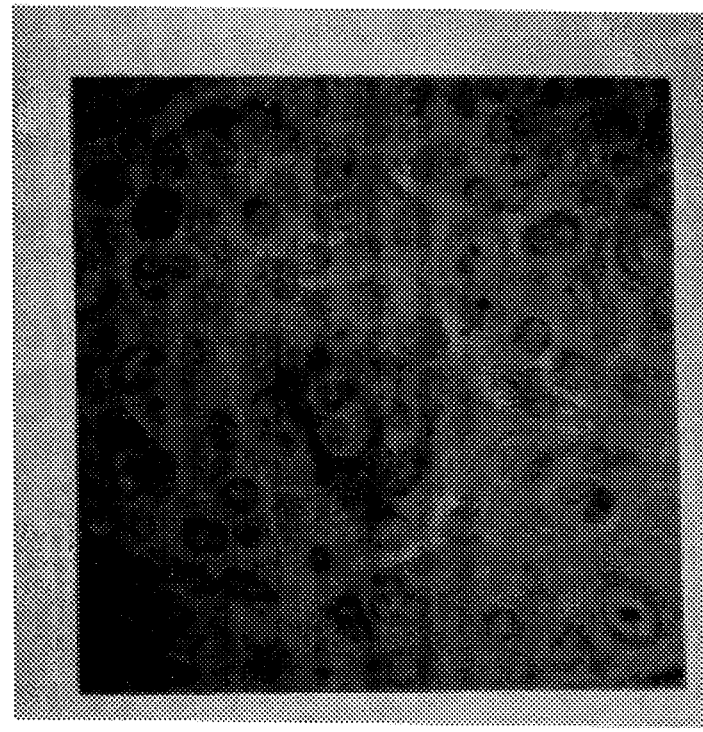
FIG. 8 shows a nodular sclerosing Hodgkin's disease stained with anti-BLA-36 by the immunoperoxidase method. A Reed-Sternberg cell variant shows membrane plus diffuse cytoplasmic reactivity (B5 paraffin section; chromogen AEC solution; counterstain hematoxylin; magnification ×500).
Figure 9:
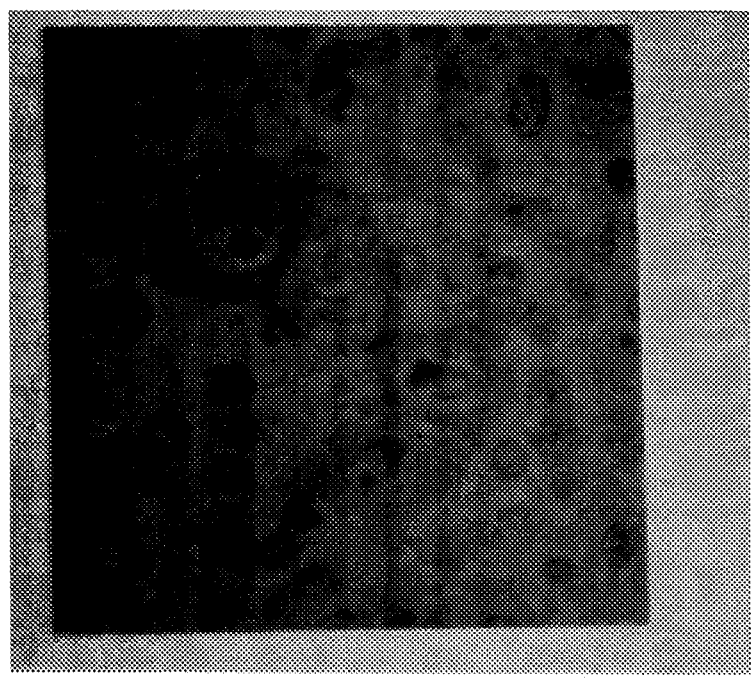
FIG. 9 illustrates a mixed cellularity Hodgkin's disease stained with anti-BLA-36 by the immunoperoxidase method. A Reed-Sternberg cell and variants show surface membrane plus focal and diffuse cytoplasmic reactivity (B5 paraffin section; chromogen AEC; counterstain hematoxylin; magnification ×500).

The results of anti-BLA-36 reactivity in 16 cases of Hodgkin's disease are shown in Table 7. A case of Hodgkin's disease was judged positive when 20% or more of Reed-Sternberg cells and variants showed reactivity with an intensity of + or greater. Classical Reed-Sternberg cells and variants including mononuclear Hodgkin's cells (256), L&H (lymphocytic and histiocytic variant) cells of the lymphocyte predominant type, lacunar cells in nodular sclerosis, pleomorphic Reed-Sternberg cells in lymphocyte depletion and necrobiotic "mummy" cells showed strong staining in all of the cases of Hodgkin's disease that were examined. The predominant staining pattern was of strong membrane reactivity with weak to moderate diffuse cytoplasmic staining (FIGS. 7,8,9). The cytoplasmic staining was occasionally punctate and paranuclear. Anti-BLA-36 marked Hodgkin's cells more consistently and sensitively than any of the other antibodies used in this panel including Leu-M1 and Ber-H2 (Table 7). Findings in frozen sections paralleled those described for paraffin sections in terms of types of cells stained, numbers of cells stained, and intensity of staining.

TABLE 7

Summary of Patterns of Reactivity in Hodgkin's Disease and the Non-Hodgkin's Lymphomas

| Subtype | # Cases | BLA-36 | L26 | UCHL-1 | Ber-H2 | LN-1 | LeuM1 |
| --- | --- | --- | --- | --- | --- | --- | --- |
| HODGKIN'S DISEASE | | | | | | | |
| Lymphocyte predominant | 3 | 3 | 2 | 0 | 0 | 2 | 0 |
| Nodular sclerosing | 6 | 6 | 0 | 0 | 3 | 0 | 4 |
| Mixed cellularity | 5 | 5 | 3 | 0 | 4 | 4 | 4 |
| Lymphocyte depleted | 2 | 2 | 0 | 0 | 1 | 0 | 1 |
| Total | 16 | 16 | 5 | 0 | 8 | 6 | 9 |
| NON-HODGKIN'S LYMPHOMAS | | | | | | | |
| B Cell | | | | | | | |
| Small lymphocytic lymphoma | 2 | 2 | 2 | 0 | 0 | 2 | 0 |
| Mantle zone lymphoma | 3 | 1 | 3 | 0 | 0 | 2 | 0 |
| Small cleaved FCC lymphoma | 4 | 4 | 4 | 0 | 0 | 4 | 0 |
| Small non-cleaved FCC lymphoma | 3 | 3 | 3 | 0 | 0 | 2 | 0 |

TABLE 7-continued

Summary of Patterns of Reactivity in Hodgkin's Disease
and the Non-Hodgkin's Lymphomas

| Subtype | # Cases | BLA-36 | L26 | UCHL-1 | Ber-H2 | LN-1 | LeuM1 |
|---|---|---|---|---|---|---|---|
| Large non-cleaved FCC lymphoma | 6 | 6 | 6 | 0 | 0 | 5 | 0 |
| BIBS | 6 | 4 | 4 | 0 | 0 | 2 | 0 |
| Total | 24 | 20 | 22 | 0 | 0 | 17 | 0 |
| T CELL | | | | | | | |
| TIBS | 8 | 1 | 1 | 6 | 0 | 1 | 0 |
| Lymphoblastic lymphoma | 2 | 0 | 0 | 0 | 0 | 0 | 0 |
| Mycosis fungoides | 1 | 0 | 0 | 1 | 1 | 0 | 0 |
| Total | 11 | 1 | 1 | 7 | 1 | 1 | 0 |

L26

L26 stained Reed-Sternberg cells and L&H cells in two of three case of lymphocyte predominant Hodgkin's disease.

In the one non-reactive case, not only were Reed-Sternberg cells non-reactive, but B lymphocytes in residual follicles did not stain, suggesting that this finding may represent a false negative attributable to loss of antigen during processing. L26 stained Reed-Sternberg cells in three of five cases of mixed cellularity Hodgkin's disease but did not stain Hodgkin's cells in nodular sclerosis of lymphocyte depletion.

UCHL-1

This pan-T lymphocyte marker stained only scattered small lymphocytes in all cases of Hodgkin's disease.

Ber-H2

Ber-H2 recognizes the Ki-1 (CD30) antigen (48). This antibody stained Reed-Sternberg cells inconsistently in this study, but stained plasma cells strong and consistently. Thus these cells served as positive internal controls. Reed-Sternberg cells in four of five cases of the mixed cellularity type and three of six cases of nodular sclerosis type showed positive stained with Ber-H2. No lymphocyte predominant cases marked with this antibody. One case of lymphocyte depleted disease was positive, the other negative.

LN-1

Reed-Sternberg cells and L&H cells were stained in six cases, two cases of lymphocyte predominant Hodgkin's disease and four cases of mixed cellularity Hodgkin's disease.

Leu-M1

Leu-M1 stained Reed-Sternberg cells and variants in four of six cases of nodular sclerosis, one of two cases of lymphocyte depleted, and four of five cases of mixed cellularity type. Leu-M1 did not stain the Reed-Sternberg cells in cases of lymphocyte predominant Hodgkin's disease.

Non-Hodgkin's Lymphomas

Thirty-five cases were evaluated: 13 lymphomas of follicular center cell origin, two cases of small lymphoma, three cases of mantle zone lymphoma, six plasmacytoid immunoblastic sarcomas (BIBS), eight cases of T immunoblastic sarcoma (TIM), two cases of lymphoblastic lymphoma, and one case of mycosis fungoides. Twenty of these cases had been immunophenotyped with fresh frozen tissue at the time of initial diagnosis.

Anti-BLA-36

Immunoreactivity of anti-BLA-36 in a variety of non-Hodgkin's lymphomas is listed in Table 7. In cases where residual normal or benign lymphoid tissue was present, anti-BLA-36 reacted strongly with most of the follicular center cells, about 30% of mantle zone lymphocytes and with medium and large transformed lymphocytes scattered in the interfollicular regions. Anti-BLA-36 had previously been shown to react strongly with follicular center cells and mantle zone lymphocytes in normal lymphoid tissue (50).

In lymphomas of B-lymphocyte origin, the most characteristic staining pattern was moderate to strong membrane staining with weak to moderate diffuse cytoplasmic staining. Occasionally punctate paranuclear staining was seen, often superimposed upon diffuse cytoplasmic staining.

Figure 10:
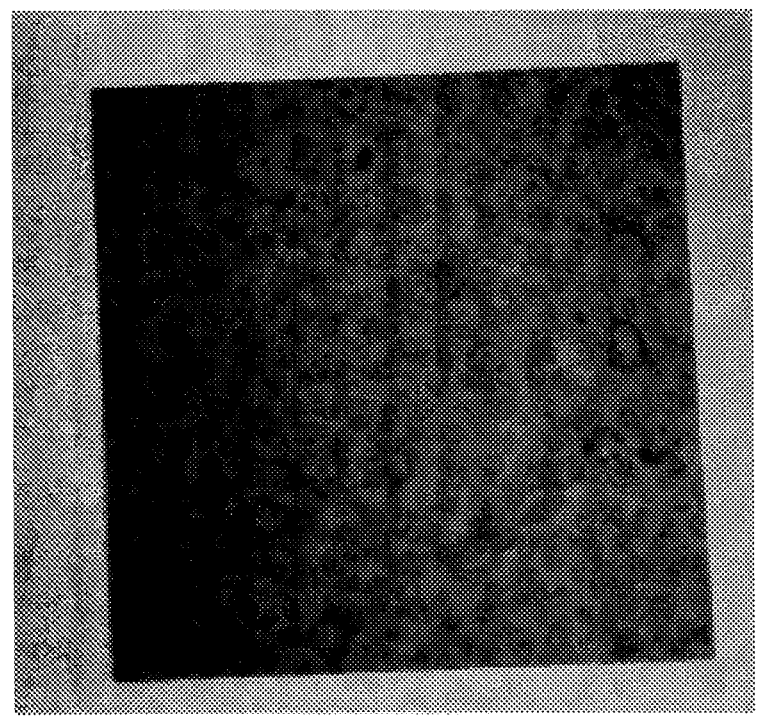
FIG. 10 illustrates a small lymphocytic lymphoma, B cell type stained with anti-BLA-36 by the immunoperoxidase method. Small lymphocytes are largely non-reactive, while scattered or focally aggregated partially transformed lymphocytes show distinct surface membrane staining (B5 paraffin section; chromogen AEC; counterstain hematoxylin; magnification ×330).

Overall, larger lymphoid cells stained with anti-BLA-36, whereas small lymphocytes did not. Thus, the mature small lymphocytes of small lymphocytic lymphoma did not react with anti-BLA-36, but the transformed lymphocytes in the proliferation centers (pseudofollicles) of small lymphocytic lymphoma stained strongly (FIG. 10). Similarly in the mantle zone and follicular center cell lymphomas, stained was most evident in the larger cell components that formed a variable part of these tumors.

Figure 11:
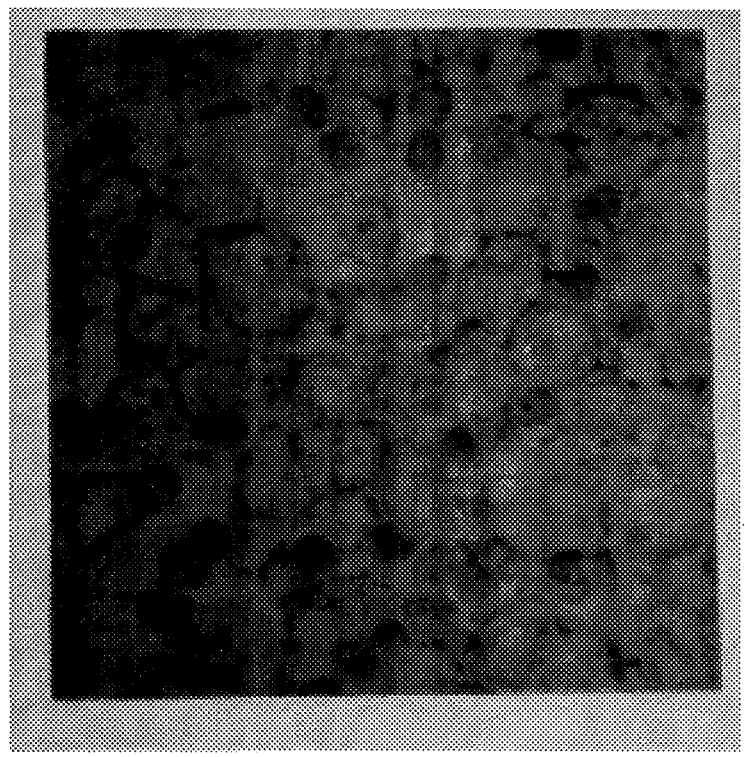
FIG. 11 shows a large non-cleaved follicular center (B) cell lymphoma stained with anti-BLA-36 by the immunoperoxidase method. The large lymphoma cells show surface membrane reactivity (B5 paraffin section; chromogen AEC; counterstain hematoxylin, magnification ×500).

In cases of large cell lymphoma derived from follicular center cells, the neoplastic lymphocytes marked moderately to strongly (FIG. 11). Four cases of plasmacytoid immunoblastic lymphoma showed strong staining of the tumor cells; two cases failed to show definite positivity. In one of these cases, all antibodies tested were non-reactive, and morphologic examination suggested inadequate fixation. In the remaining case, BLA-36 was judged non-reactive, while L26 stained approximately 10% of the tumor cells.

Anti-BLA-36 was judged non-reactive in 10 of the 11 T-cell lymphomas. One case of TIBS showed positivity of approximately 30% of cells for BLA-36 and 15% for L26. This case was recorded as a positive case in Table 7. A second case showing approximately 10% of cells reactive with anti-BLA-36 and L25 was listed as negative in accordance with the criteria set forth under methods. In both of these cases, UCHL-1 (anti-T cell) stained many small lymphocytes and scattered larger cells. Frozen section immunotyping was not available in the first of these cases and was inconclusive in the second; classification of these cases had therefore been based primarily on morphology.

L26

L26 stained the great majority of all B lymphocytes in benign and neoplastic conditions. This held true across the spectrum of B-lymphocyte neoplasms. L26 failed to stain T-lymphocyte lymphomas in all cases but one: as noted above, this case also showed some positivity for BLA.26 and previous attempts at establishing an immunophenotype has been inconclusive. Likewise, L26 did not stain T-lymphocyte zones in benign areas of any lymph node evaluated in the study.

UCHL-1

UCHL-1 stained only scattered small lymphocytes in the neoplasms of B-lymphocyte origin. Six of the eight cases designated as TIBS showed positivity of large apparently neoplastic cells; in the other two cases only small lymphocytes stained convincingly.

LN-1

LN-1 marked the neoplastic lymphocytes in 11 of 13 follicular center cell lymphomas, plus two of three mantle zone lymphomas and the "pseudo follicle" cells of both cases of small lymphocytic lymphoma. Two of six cases of BIBS were positive, while rare positive cells were observed in one of eight cases of TIBS. Benign follicular center cells stained strongly in those cases with residual follicles.

Ber-H2 and Leu-M1

These two antibodies contributed little to the evaluation of the B-lymphocyte lymphomas. Ber-H2 stained plasma cells, and Leu-M1 strongly stained scattered granulocytes, neither of which finding contributed to diagnostic evaluation. Cases of Ber-H2 (Ki-1)-positive large cell lymphomas were not encountered in this study.

C. Discussion

Morphological and immunohistochemical studies suggest that lymphocyte predominant Hodgkin's disease is a B-cell neoplasma and as such is distinct from other subtypes of Hodgkin's disease (51,57–65). This view derives at least in part from the observation that the Reed-Sternberg cells and L&H cells of this subtype of Hodgkin's disease react with B-lymphocyte markers such as L26 (51,52), KiB3 (60), LN-1 (47,53), B1, Leu 14 and Dapo pan-B (64), but not with other antibodies such as Leu-M1 (24) or Ber-H2 (53) that do not stain B cells. Conversely, Reed-Sternberg cells and variants in the other subtypes of Hodgkin's disease typically do not stain with antibodies that mark B cells, but do stain with Leu-M1 (24) and Ber-H2 antibodies (53). In the present study, anti-BLA-36, a marker of certain B lymphocytes and B cell lymphomas (49,50), stained Reed-Sternberg cells and variants consistently in all four subtypes of Hodgkin's disease.

The findings of this study are in accord with several recent lines of evidence accumulating from clinical (63,66), immunohistochemical (47,51,53,57) and gene rearrangement studies (68,69) which offer some support for the concept that, at least in some instances, the Reed-Sternberg cell may be derived from a cell in common lineage with the B lymphocyte. As noted above, the lymphocyte predominant subtype, possibly the most differentiated form of Hodgkin's disease (70), appears to be derived from B lymphocytes based on morphological (57,60,63,64) and immunohistochemical (47,51,53) characteristics. In addition, progressive transformation of germinal centers commonly occurs in association with, or may precede the development of, lymphocyte predominant Hodgkin's disease (57–62,71). Clonal rearrangements of immunoglobulin heavy or light chain genes have been found in tissue samples, rich in Reed-Sternberg cells, from patients with other subtypes of Hodgkin's disease (68,69), an observation consistent with a B-lymphocyte origin for the Reed-Sternberg cell. Clinicopathologic evidence for a B-cell origin of Reed-Sternberg cells takes the form of rare occurrences of lymphomas in which both Hodgkin's disease and non-Hodgkin's lymphoma (composite lymphomas) are found in the same lymph node group (66,72,73). In these cases, the non-Hodgkin's lymphoma is usually a B-cell neoplasm. Moreover, the co-existence of a large cell lymphoma of B-cell origin is especially common with lymphocyte predominant Hodgkin's disease (66).

Finally, a recent report demonstrating Epstein-Barr virus (EBV) genomes within Reed-Sternberg cells gives credence to the notion that Reed-Sternberg cells may be of B-lymphocyte lineage (74). C3d, which is found on most mature B cells, is identical to the receptor for EBV; thus, B cells ate the usual human host cell for EBV (75).

The present work identified a monoclonal antibody raised to a Hodgkin's disease cell line that also detects a protein expressed on early B cells and on activated B cells. As far as we are aware, this is the first antibody raised to a Hodgkin's cell line which also reacts with benign and malignant B lymphocytes. Other antibodies that have been found to stain both Reed-Sternberg cells and B cells have been raised against B cells, e.g., L26 (52,76), LN-1 and LN-2 (17), EPB-1 (77). The reciprocal nature of this reactivity may provide evidence linking the Reed-Sternberg cell and the B lymphocyte. The BLA-36 is expressed on early B cells and activated B cells (but not resting or peripheral blood B cells). It is also present on the surface of Reed-Sternberg cells and their mononuclear variants, often referred to as Hodgkin's cells (25). However, the significance of BLA-36 expression in cellular function, or in terms of elucidating the origin of the Reed-Sternberg cell, still is not entirely known. We have shown (49,50) that addition of anti-BLA-36 antibody to in vitro cultures of B cells, B cell lines, or Hodgkin's lines produces an immediate, but reversible, inhibition of cell division, with a less immediate and less profound suppression of DNA synthesis, as measured by uptake of tritiated thymidine (50). It is tempting, therefore, to speculate that BLA-36 may subserve the function of a cell surface receptor for an as yet unknown growth factor.

Apart from the implications anti-BLA-36 may have in exploring B-cell proliferation or in delineating the origin of the Reed-Sternberg cell, this study demonstrates that, on a more practical level, anti-BLA-36 is of value in the identification of Reed-Sternberg cells in all four major types of Hodgkin's disease. It is specific and sensitive, and it has the advantage of being effective in B5-fixed paraffin-embedded material. Anti-BLA-36 may be of particular value in differentiating between lymphocyte predominant Hodgkin's disease and other benign and malignant lymphoproliferative disorders, including small lymphocytic lymphoma, T-zone hyperplasia, sarcoidosis, progressive transformation of germinal centers, and giant lymph node hyperplasia. The key to the histopathological differential is identifying the presence of rare Reed-Sternberg and L&H cells. The combination of immunohistological staining for BLA-36 and the excellent morphology of B5- or formalin-fixed paraffin-embedded sections facilitates recognition of L&H cells and Reed-Sternberg cells and permits their distinction from any positively stained transformed B lymphocytes which may be encountered in conditions other than Hodgkin's disease.

Anti-BLA-36 may also have a role in the evaluation of B-cell lymphomas and their distinction from T-cell processes. Those B-cell lymphomas with a predominant large cell component (large non-cleaved follicular center cell lymphoma and BIBS) are mostly positive (10 or 12), while large cell lymphomas of T-cell type (TIBS) are mostly negative (7 of 8). Furthermore, review of the discrepant cases raised doubts as to the validity of the original diagnoses that had been made in the absence of conclusive immunologic data. In B-cell lymphomas composed of smaller cells, anti-BLA-36 serves to highlight the presence of foci of larger transformed lymphocytes (pseudofollicles) in small lymphocytic lymphoma, and reveals minority populations of large follicular center cells or follicle structures in small cleaved cell lymphoma, thereby abetting the diagnosis of these conditions.

With regard to other antibodies employed in this study, we noted that L26, a widely used pan-B cell marker, reacted with B cells in most cases of non-Hodgkin's lymphoma, thereby showing considerable overlap with anti-BLA-36. However, L26 stained Reed-Sternberg cells and variants in only 5 of 16 cases of Hodgkin's disease. The limited ability of L26 to stain Reed-Sternberg cells in Hodgkin's disease, other than lymphocyte predominant type, is in agreement with the experience of others (51). The failure of L26 to stain the Reed-Sternberg cells and L&H cells in one of our cases of lymphocyte predominant Hodgkin's disease is at variance with a report by Pinkus and said (51) describing uniform reactivity of L26 in this condition. A possible explanation for this discrepancy may related to accidental destruction of antigen during tissue processing, since residual B cells in this case also were non-reactive for L26.

We found other minor discrepancies with published reports. Hsu et al (23) described positivity for LeuM1 in Reed-Sternberg cells of all 20 cases of Hodgkin's disease that they studied; we observed positivity in 9 of 13, excluding the lymphocyte predominant subtype. Other investigators have reported positivity for LeuM1 of approximately 90% (24,53). There appears to be uniform agreement that the Reed-Sternberg cells and variants of lymphocyte predominant Hodgkin's disease are nonreactive for LeuM1. LN-1 was positive in Reed-Sternberg cells of 6 of 16 cases in our series, approximately 30% of cases in the series described by Chittal and colleagues (53) and 28% of the cases in the earlier publications on LN-1 by Sherrod et al (47). Finally, in the present study we observed Ber-H2 positivity in Reed-Sternberg cells in 8 of 16 cases; Chittal and colleagues (53) reported positivity in 75% of their cases, while Stein and collaborators in an earlier report (67) cited positivity for Ki-1 in 100% of cases. The consensus appears to be that lymphocyte predominant disease is least often positive for Ki-1 (or Ber-H2) [Chittal et al: 3 of 18 (53)]. In our series all of our Ber-H2 (Ki1) positive cases were in the nodular sclerosis, mixed cellularity or lymphocyte depleted category for an overall positivity rate of 69%.

These findings extend the essentials of our previous report (50) that revealed BLA-36 positivity in Reed-Sternberg cells of 28 of 28 cases of Hodgkin's disease and 23of 25 cases of B-cell lymphoma. Furthermore, anti-BLA-36 was considered to be distinct from other human anti-leukocyte antibodies, a conclusion supported by the present study. These results provide further incentive for additional studies of the diagnostic utility of this antibody. Recognition of a cell surface antigen restricted to B cells and Reed-Sternberg cells also raises the possibility of the use of anti-BLA-36 for imaging and radio-immunotherapy of B-cell lymphomas and Hodgkin's disease.

Notwithstanding that reference has been made to particular preferred embodiments, it will be understood that the present invention is not to be construed as limited to such, rather to the lawful scope of the appended claims.

REFERENCES

1. Stein, et al., *Int. J. Cancer* 29, 283–290 (1982).
2. Hecht, et al., *J. Immunol* 134, 4231–4236 (1985).
3. Taylor, C. R., *Annual Research Reviews*, Churchill Livingston/Eden Press (1980).
4. Taylor, C. R., *Controversies in the Management of Lymphomas II*, Martinus Nijhoff Publishers, pp. 91–110 (1983).
5. Taylor, C. R. *Recent Results Cancer Res.* 64, 214–231 (1978).
6. Jones, et al., *Hematol. Oncol.* 3, 133–145 (1985).
7. Diehl, et al., *J. Cancer Res. Clin. Oncol.* 101, 111–124 (1981).
8. Poppema, et al., *Cancer* 55, 683–690 (1985).
9. Minowada, et al., *Proc. 10th Intl. Res. Congress*, 108–112 (1984).
10. Kohler, et al., *Nature* (Lond.) 256, 495–497 (1975).
11. Imam, et al., *Cancer Res.* 45, 263–271 (1985).
12. Parham, P., *J. Immunol.* 131, 2895–2902 (1983).
13. Abrahamson, et al. *J. Immunol.* 126, 83–88 (1981).
14. Kersey, et al., *J. Exp. Med.* 153, 726–731 (1981).
15. Stashenko, et al., *J. Immunol.* 125, 1678–1685 (1980).
16. Nadler, et al., *J. Immunol.* 131, 244–250 (1983).
17. Epstein, et al., *J. Immunol.* 133, 1028–1036 (1984).
18. Imam, et al., *Cancer Invest.* 3, 339–359 (1984).
19. Laemli, U. K., *Nature* (Lond.) 227, 680–685 (1970).
20. Towbin, et al., *Proc. Natl. Acad. Sci. USA* 76, 4350–4355 (1979).
21. Murphy, et al., *Biochim. Biophys. Acta* 420, 87–96 (1976).
22. Tarentino, et al., *J. Biol. Chem.* 249, 818–824 (1974).
23. Hsu, et al., *Am. J. Clin. Pathol.* 82 29–32 (1984).
24. Pinkus, et al., *Am. J. Pathol.* 119 244–252 (1985).
25. Moeschlin, et al., *Schweiz Med. Wschr.* 80, 1103–1106 (1950).
26. Marder, et al., *Lab. Invest.* 52, 497–504 (1985).
27. Bhoopat, et al., *Bloos* 71, 1079–1085 (1988).
28. Epstein, et al., *Blood* 70, 1124–1130 (1987).
29. Nadler, et al., *Bl. J. Immunol.* 126, 1941–1947 (1981).
30. Knowles II, et al., *Blood* 62, 191–199 (1983).
31. Frisman, et al., *Blood* 62, 1224–1229 (1983).
32. Hofman, et al., *Blood* 62, 775–783 (1983).
33. Yokochi, et al., *J. Immunol.* 128., 823–827 (1982).
34. Thorley-Lawson, et al., *Cell* 30, 415–425 (1982).
35. Shipp, et al., *J. Immunol.* 131, 2458–2467 (1983).
36. Zola, et al., *Clin. Exp. Immunol.* 52, 655–664 (1983).
37. Funderud, et al., *Scand. J. Immunol.* 17, 161–169 (1983).
38. Mittler, et al., *J. Immunol.* 131, 1754–1761 (1983).
39. Forster, et al., *Cancer Res.* 42, 1927–1934 (1982).
40. Wiels, et al., *Proc. Natl. Acad. Sci. USA* 78, 6485–6488 (1981).
41. Anderson, et al., *J. Immunol.* 130, 1132–1138 (1983).
42. Hofman, et al., *J. Immunol.* 133, 1197–1201 (1984).
43. Clark, et al., *Proc. Natl. Acad. Sci. USA* 82, 1766–1770 (1985).
44. Golay, et al., *J. Immunol.* 135, 3795–3801 (1985).
45. Tubbs, et al., *Semin. Diag. Pathol.* 1, 272–284 (1984).
46. Taylor, C. R., "A Tool for the Surgical Pathologist", W. B. Saunders (1986).
47. Sherrod, et al., *Cancer* 57, 2135–2140 (1986).
48. Schwarting, et al., *J. Immunol.*, in press.
49. Imam, et al., *Ann. NY Acad. Sci.* 551, 363–365 (1988).
50. Imam, et al., "Characterization of a developmentally associated molecule expressed on B and Hodgkin's cells", in press.
51. Pinkus, et al., *Am. J. Pathol.* 133, 211–217 (1988).
52. Cantun, et al., *Am. J. Pathol.* 129, 415–421 (1987).
53. Chittal, et al., *Am. J. Surg. Pathol.* 12, 9–21 (1988).
54. Norton, et al., *J. Clin. Pathol.* 39, 399–405 (1986).
55. Lukes, et al., *Cancer Res.* 26, 1311 (1966).
56. National Cancer Institute, *Cancer* 49, 2112–2135 (1982).
57. Burns, et al., *Am. J. Surg. Pathol.* 8, 253–261 (1984).
58. Poppema, et al., *Virchows Arch. B Cell. Pathol.* 31, 211–225 (1979).
59. Timens, et al., *Lab. Invest,* 54, 457–461 (1986).
60. Hansmann, et al., *Virchows Arch. Pathol. Anat.* 409, 171–181 (1986).
61. Hansmann, et al., *J. Cancer Res. Clin. Oncol.* 114, 405–410 (1988).
62. Crossley, et al., *Histopathology* 11, 621–630 (1987).
63. Osborne, et al., *Am. J. Surg. Pathol.* 8, 725–733 (1984).
64. Pinkus, et al., *Am. J. Pathol.* 119, 244–252 (1985).
65. Abdulazziz, et al., *Histopathology* 8, 1–25 (1984).

66. Sundeen, et al., *Am. J. Surg. Pathol.* 12, 599–606 (1988).
67. Stein, et al., *Blood* 66, 848–858 (1985).
68. Sundeen, et al., *Blood* 70, 96–103 (1987).
69. Weiss, et al., *Hum. Pathol.* 17, 1009–1014 (1986).
70. Grogan, et al., "Surgical Pathology of the Lymph Nodes and Related Organs", W. P. Saunders (1985).
71. Lennert, et al., *Am. J. Surg. Pathol.* 11, 149–150 (1987).
72. Kim, et al., *Cancer* 40, 959–976 (1977).
73. Van den Tweel, et al., *Am. J. Clin. Pathol.* 71, 509–520 (1977).
74. Weiss, et al., *N. Engl. J. Med.* 320, 502–506 (1989).
75. Fingeroth, et al., *Proc. Natl. Acad. Sci. USA* 81, 4510–4514 (1984).
76. Ishii, et al., *Clin. Exp. Immunol.* 58 183–192 (1984).
77. Pawlak-Byczkowska, et al., *Cancer Res.* 49, 4568–4577 (1989).

We claim:

1. An antibody or fragment thereof which specifically binds B lymphocyte antigen 36 (BLA-36), said BLA-36 being an antigen expressed on the cell membrane of Hodgkin's cells, Reed-Sternberg cells and B cells, and being characterized as having a molecular weight of 36 kD as assessed by SDS-PAGE.

2. Monoclonal antibody according to claim 1, which is labeled.

3. A hybridoma cell line producing antibody according to claim 1.

4. A method for screening for Hodgkin's disease or B cell lymphoma in a mammal, comprising the steps of:
    obtaining antibody which specifically binds B lymphocyte antigen protein 36 (BLA-36), said BLA-36 being an antigen expressed on the cell membrane of Hodgkin's cells, Reed-Sternberg cells and B cells, and being characterized as having a molecular weight of 36 kD as assessed by SDS-PAGE;
    contacting said antibody with tissue or cells obtained from said mammal to be diagnosed; and
    detecting the antigen protein, if present, wherein the detection of the antigen protein indicates the presence of Hodgkin's Disease or B cell lymphoma.

5. The method according to claim 4 wherein said antibody is in the form of an enzyme-antibody conjugate.

6. The method according to claim 5 wherein said antigen protein is detected by enzyme-linked immunosorbent assay (ELISA).

7. Assay kit for the detection of B lymphocyte antigen protein 36 (BLA-36), in mammalian tissues or cells in order to screen for Hodgkin's disease or B cell lymphoma, said BLA-36 being an antigen expressed on the cell membrane of Hodgkin's cells, Reed-Sternberg cells and B cells, and being characterized as having a molecular weight of 36 kD as assessed by SDS-PAGE, said kit comprising an antibody which specifically binds said antigen protein and means for indicating the reaction of said antibody with said antigen, if present.

8. The antibody of claim 1, wherein said antibody is a monoclonal antibody.

9. The method of claim 4, wherein said antibody is a monoclonal antibody.

10. The assay kit of claim 7, wherein said antibody is a monoclonal antibody.

11. The assay kit of claim 7, wherein said antibody which specifically binds said antigen is labeled.

12. The assay kit of claim 7, wherein said antibody is an unlabeled first antibody and said means for indicating the reaction comprises a labeled second which is anti-immunoglobulin.

13. The assay kit of claim 11, wherein the antibody which specifically binds said antigen is labeled with a marker selected from the group consisting of a fluorochrome, an enzyme, a Radionuclide and a radiopaque material.

14. The assay kit of claim 12, wherein the second antibody is labeled with a marker selected from the group consisting of a fluorochrome, an enzyme, a radionuclide and a radiopaque material.

* * * * *